US008508727B2

(12) United States Patent
Uto et al.

(10) Patent No.: US 8,508,727 B2
(45) Date of Patent: Aug. 13, 2013

(54) DEFECTS INSPECTING APPARATUS AND DEFECTS INSPECTING METHOD

(75) Inventors: Sachio Uto, Yokohama (JP); Minori Noguchi, Yokohama (JP); Hidetoshi Nishiyama, Yokohama (JP); Yoshimasa Ohshima, Yokohama (JP); Akira Hamamatsu, Yokohama (JP); Takahiro Jingu, Tokyo (JP); Toshihiko Nakata, Yokohama (JP); Masahiro Watanabe, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/529,363

(22) Filed: Jun. 21, 2012

(65) Prior Publication Data

US 2012/0262709 A1    Oct. 18, 2012

Related U.S. Application Data

(63) Continuation of application No. 13/221,935, filed on Aug. 31, 2011, now Pat. No. 8,228,495, which is a continuation of application No. 12/823,510, filed on Jun. 25, 2010, now Pat. No. 8,013,989, which is a continuation of application No. 12/192,578, filed on Aug. 15, 2008, now Pat. No. 7,768,634, which is a continuation of application No. 10/536,715, filed on Oct. 21, 2005, now Pat. No. 7,417,721.

(30) Foreign Application Priority Data

Nov. 27, 2002 (JP) ................................. 2002-344327

(51) Int. Cl.
*G01N 21/00* (2006.01)

(52) U.S. Cl.
CPC ...................................... *G01N 21/00* (2013.01)
USPC .................... 356/237.2; 356/237.3; 356/237.4

(58) Field of Classification Search
CPC ...................................................... G01N 21/00
USPC .......................................... 356/237.1–237.5
See application file for complete search history.

(56) References Cited

U.S. PATENT DOCUMENTS

| 5,225,886 | A |   | 7/1993  | Koizumi et al. |           |
|-----------|---|---|---------|----------------|-----------|
| 5,233,191 | A |   | 8/1993  | Noguchi et al. |           |
| 5,274,434 | A |   | 12/1993 | Morioka et al. |           |
| 5,293,538 | A | * | 3/1994  | Iwata et al.   | 356/239.1 |
| 5,424,536 | A |   | 6/1995  | Moriya         |           |
| 5,463,459 | A |   | 10/1995 | Morioka et al. |           |
| 5,623,340 | A | * | 4/1997  | Yamamoto et al.| 356/237.4 |
| 5,699,153 | A | * | 12/1997 | Takamoto et al.| 356/237.1 |

(Continued)

FOREIGN PATENT DOCUMENTS

| JP | 62-089336  | 4/1987 |
|----|------------|--------|
| JP | 63-135848  | 6/1988 |

(Continued)

*Primary Examiner* — Michael P Stafira
(74) *Attorney, Agent, or Firm* — Antonelli, Terry, Stout & Kraus, LLP.

(57) ABSTRACT

An inspecting apparatus and method including first and second illuminating units for illuminating a surface of a specimen to be inspected with different incident angles and first and second detecting optical units arranged at different elevation angle directions to the surface of the specimen for detecting images of the specimen illuminated by the first and second illuminating units.

18 Claims, 30 Drawing Sheets

(56) References Cited

U.S. PATENT DOCUMENTS

| | | | |
|---|---|---|---|
| 5,936,726 A | 8/1999 | Takeda et al. | |
| 6,512,578 B1 * | 1/2003 | Komatsu et al. | 356/237.5 |
| 6,587,193 B1 * | 7/2003 | Reinhron et al. | 356/237.5 |
| 6,894,302 B2 * | 5/2005 | Ishimaru et al. | 250/559.46 |
| 7,417,721 B2 | 8/2008 | Uto et al. | |
| 8,013,989 B2 | 9/2011 | Uto et al. | |

FOREIGN PATENT DOCUMENTS

| | | |
|---|---|---|
| JP | 01-117024 | 5/1989 |
| JP | 01-250847 | 10/1989 |
| JP | 05-129399 | 5/1993 |
| JP | 06-242012 | 9/1994 |
| JP | 06-258239 | 9/1994 |
| JP | 06-324003 | 11/1994 |
| JP | 07-083840 | 3/1995 |
| JP | 08-210989 | 8/1996 |
| JP | 8-271437 | 10/1996 |
| JP | 11-237344 | 8/1999 |
| JP | 2000-105203 | 4/2000 |
| JP | 2000-162141 | 6/2000 |
| JP | 2001-060607 | 3/2001 |
| JP | 2001-264264 | 9/2001 |

* cited by examiner

|  |  | PROCESS BY 1×1 PIXEL | |
|---|---|---|---|
|  |  | DETECTION | NON-DETECTION |
| PROCESS BY 5×5 PIXELS | DETECTION | LARGE FOREIGN MATTERS | FOREIGN MATTERS BEING LOW IN HEIGHT |
|  | NON-DETECTION | FINE FOREIGN MATTERS | — |

FIG.19(a)
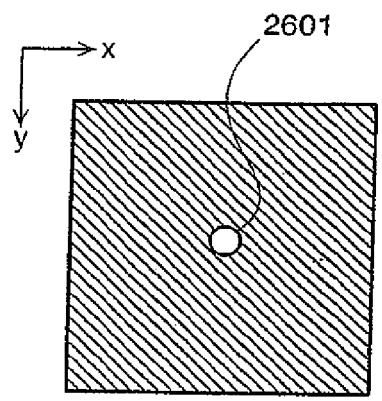
FIG. 19(b)
| 0 | 0 | 0 | 0 | 0 | 0 | 0 | 0 | 0 |
|---|---|---|---|---|---|---|---|---|
| 0 | 0 | 0 | 0 | 0 | 0 | 0 | 0 | 0 |
| 0 | 0 | 0 | 0 | 10 | 0 | 0 | 0 | 0 |
| 0 | 0 | 0 | 10 | 45 | 8 | 0 | 0 | 0 |
| 0 | 0 | 0 | 18 | 255 | 23 | 0 | 0 | 0 |
| 0 | 0 | 3 | 24 | 255 | 59 | 17 | 0 | 0 |
| 0 | 0 | 0 | 4 | 33 | 30 | 6 | 0 | 0 |
| 0 | 0 | 0 | 0 | 5 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
FIG.20
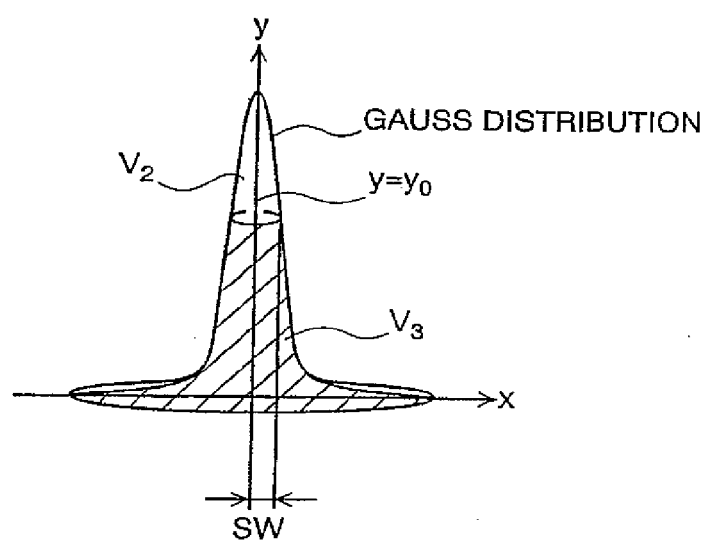

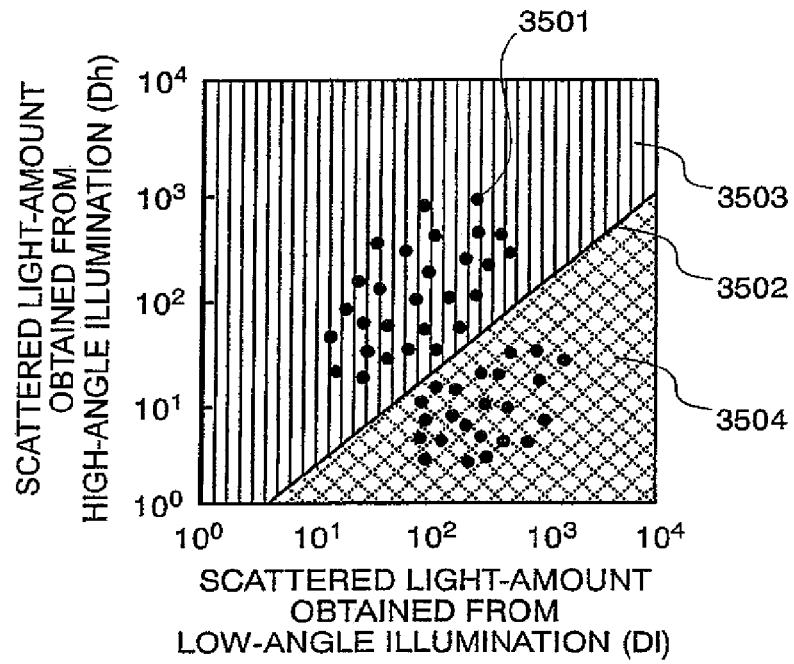
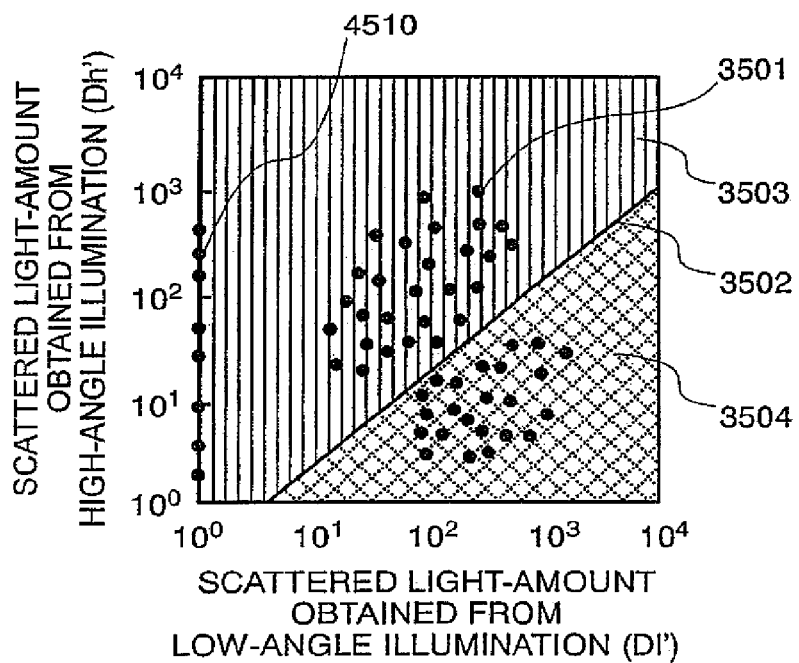

DEFECTS INSPECTING APPARATUS AND DEFECTS INSPECTING METHOD

CROSS REFERENCE TO RELATED APPLICATION

This application is a continuation application of U.S. application Ser. No. 13/221,935, filed Aug. 31, 2011, which is a continuation of U.S. application Ser. No. 12/823,510, filed Jun. 25, 2010, which is now U.S. Pat. No. 8,013,989, issued Sep. 6, 2011, which is a continuation of U.S. application Ser. No. 12/192,578, filed Aug. 15, 2008, which is now U.S. Pat. No. 7,768,634, issued Aug. 3, 2010, which is a continuation of U.S. application Ser. No. 10/536,715, filed with a 35 U.S.C. §371 national stage filing date of Oct. 21, 2005, and is now U.S. Pat. No. 7,417,721, issued Aug. 26, 2008, the contents of which are incorporated herein by reference.

FIELD OF THE INVENTION

The present invention relates to a defects inspecting apparatus for detecting defects, such as, foreign matters or particles (hereinafter, "foreign matters", collectively), existing upon a thin-film substrate, a semiconductor substrate and/or a photo mask, etc., in particular, when manufacturing a semiconductor chip and/or a liquid crystal product, or scratches or the like, which are caused on a circuit pattern, thereby inspecting a situation of generating such foreign matters or the like, within a manufacturing process of devices, for analyzing the defects, such as, the foreign matters, etc., which are detected, as well as, a method thereof.

BACKGROUND OF THE INVENTION

Within the manufacturing process of semiconductors, presence of the foreign matters on a semiconductor substrate (i.e., a wafer) comes to be a cause of generation of defects, such as, insulation failure (or, ill insulation) or short-circuiting between wiring patterns, etc. Further, accompanying with miniaturization of the semiconductor elements, such the foreign matters, but being fine or microscopic much more, also comes to be the reason of ill insulation of a capacitor and/or breakage of gate oxidization films, etc. Thus, such the foreign matters, including those generated from movable portions of a conveyer, those generated from a human body, those produced by processing gas through reaction thereof within a processing apparatus, and those mixed within chemicals and materials, for example; they are mixed up with one another, under various conditions and due to various kinds of reasons thereof.

In the similar manner, within the manufacturing process of a liquid crystal display device, the device results into the useless if generating any kind of defects therein, such as, mixture of foreign matters in the patterns thereon, for example. Also, being similar in the condition mentioned above, within the manufacturing process of a printed circuit board, mixture of the foreign matters also results into short-circuiting and/or ill connection of patterns thereon.

As one of such technologies relating to the conventional arts, for detecting the foreign matters on the semiconductor substrate, for example, in Japanese Patent Laying-Open No. Sho 62-89336 (1987) <Conventional Art 1>, there is disclosed a technology of detecting lights scattered from foreign matters while irradiating a laser beam thereupon, being generated in a case when the foreign matters adhere upon the semiconductor substrate, and then making comparison thereof, with using the results of inspection obtained previously, upon the same king of semiconductor substrate, so as to neglect a false report due to the patterns thereon; thereby, enabling an inspection of foreign matters and defects with high sensitivity and high reliability. Also, as is disclosed in Japanese Patent Laying-Open No. Sho 63-135848 (1988) <Conventional Art 2>, for example, there is also known a technology of detecting lights scattered from foreign matters while irradiating a laser beam thereupon, being generated in a case when the foreign matters adhere upon the surface of semiconductor substrate, and then analysis is made upon the foreign matter detected, through the analyzing technology, such as, the laser photoluminescence or the secondary X-ray analysis (XMR), etc.

Also, as a technology for inspecting the above-mentioned foreign matters, there is disclosed a method of removing the lights emitted from repetitive patterns upon a wafer when irradiating coherent lights upon the wafer through a space filter(s), thereby detecting the foreign matters and/or defects having no such repetitiveness, with emphasis thereof. Further, a foreign matter inspecting apparatus is also already known, for example, in Japanese Patent Laying-Open No. Hei 1-117024 (1989) <Conventional Art 3>, in which apparatus a light is irradiated upon circuit patterns formed on a wafer from a direction inclined by 45 degree with respect to a group of main lines of the said circuit patterns, thereby preventing the $0^{th}$-order diffracted light from entering into an opening of an objection lens. Moreover, as the conventional technologies relating to a defects inspecting apparatus and a method thereof, for inspecting foreign matters, etc., there are also already known the followings: Japanese Patent Laying-Open No. Hei 1-250847 (1989) <Conventional Art 4>; Japanese Patent Laying-Open No. Hei 6-258239 (1994) <Conventional Art 5>; Japanese Patent Laying-Open No. Hei 6-324003 (1994) <Conventional Art 6>; Japanese Patent Laying-Open No. Hei 8-210989 (1996) <Conventional Art 7>; Japanese Patent Laying-Open No. Hei 8-271437 (1996) <Conventional Art 8>; and Japanese Patent Laying-Open No. 2000-105203 (2000) <Conventional Art 9>. In particular, the conventional technology 9 describes that a size of detecting pixel can be changed through exchanging a detection optic system. Also a technology for measuring a size of foreign matter is disclosed in Japanese Patent Laying-Open No. 2001-60607 (2001) <Conventional Art 10> and Japanese Patent Laying-Open No. 2001-264264 (2001) <Conventional Art 11>, for example.

DISCLOSURE OF THE INVENTION

However, with the Conventional Arts 1 through 9, it is impossible to detect the fine or microscopic foreign matters, or defects upon the substrate, easily, on which repetitive patterns and non-repetitive patterns are formed mixing with each other, at high sensitivity and at high speed. Thus, with those Conventional Arts 1 through 9 mentioned above, in particular, in a portion other than the repetitive portion, such as, a cell portion of a memory, for example, there is a problem that the detection sensitivity is low (i.e., the minimum size of a detectable foreign matter is large). Also, with the Conventional Arts 1 through 9 mentioned above, there is other problem that the detection sensitivity is low on the fine foreign matters or defects, such as, a level of 0.1 μm, in particular, within a region where the pattern density is high. Further, with the Conventional Arts 1 through 9 mentioned above, there is other problem that the detection sensitivity is also low, in particular, on the foreign matters or defects, which build up short-circuiting between the wiring patterns, or on a film-like defects. Or, with the Conventional Arts 10 and 11 mentioned above, there is a problem that accuracy is low, in particular, when measuring the foreign matters or the defects. Also, with the Conventional Arts 10 and 11 mentioned above, there is another problem that the sensitivity is low when detecting the foreign matters upon the wafer surface, on which a transparent thin film is formed.

A first object, according to the present invention, for dissolving such the problem (s) as was mentioned above, is to provide a defects inspecting apparatus and a method thereof, enabling to make inspection at high sensitivity and further at high speed, about the defects, such as, fine or microscopic foreign matters and/or scratches, etc., of a level 0.1 µm, upon a substrate of inspection target, such as, a wafer, for example, having circuit patterns formed thereon, as well as, the inspection target substrate, on a surface of which the transparent thin film (s) is/are formed.

Also, a second object is, according to the present invention, to provided a defects inspecting apparatus and a method thereof, enabling to make an inspection about the foreign matters or defects, at high sensitivity, even in an area or region where the pattern density is high.

Also, a third object is, according to the present invention, to provided a defects inspecting apparatus and a method thereof, enabling to make an inspection about the foreign matters, short-circuiting between the wiring patterns, or thin film-like defects, at high sensitivity.

And further, a fourth object is, according to the present invention, to provide a defects inspecting apparatus and a method thereof, enabling classification of the foreign matters and defects existing upon the inspection target substrate.

For accomplishing the object(s) mentioned above, according to the present invention, first there is provided a defects inspecting apparatus, comprising: a scanning stage for running into a predetermined direction while mounting an inspection target substrate thereon; an illumination optic system for irradiating an illumination light beam upon a surface of said inspection target substrate at a predetermined angle inclined thereto; a detection optic system including, an upper-directed detection optic system, having an objection lens for condensing upper-directed reflected/diffracted lights reflected and/or diffracted upwards from said inspection target substrate, an upper-directed image-forming optic system for forming an image of the upper-directed reflected/diffracted lights condensed through said objection lens, and an upper-directed photo-detector for receiving the image of the upper-directed reflected/diffracted lights, which is formed through said upper-directed image-forming optic system, and thereby converting into an upper-directed image signal, and a side-directed detection optic system, having a side-directed image-forming optic system for forming an image through condensing side-directed reflected/diffracted lights emitted from said inspection target substrate into a direction inclined so as to flatly intersect said illumination light beam, and a side-directed photo-detector for receiving an image of the side-directed reflected/diffracted lights, which is formed through said side-directed image-forming optic system; an A/D converter for converting the upper-directed image signal obtained from the upper-directed photo-detector of said detection optic system into an upper-directed digital image signal, and for converting the side-directed image signal obtained from said side-directed photo-detector into a side-directed digital image signal; and a signal processing system for detecting defects upon basis of each of the digital signals converted within said A/D converter.

Also, according to the present invention, said illumination light beam is made to be a slit-like beam of lights in about parallel with a longitudinal direction thereof, as an illumination condition upon said inspection target substrate, and nearly normal to the running direction of said scanning stage in the longitudinal direction thereof, within said illumination optic system.

Also, according to the present invention, the upper-directed detection optic system of said detection optic system has a space filter for shielding at least repetitive lights of circuit patterns lying on the inspection target substrate, and repetitive light shielding pattern of the space filter can be set up, automatically, in sizes and configurations thereof. Also, according to the present invention, a magnifying power of said image-forming optic system is variable, within the upper-directed detection optic system of said detection optic system.

Also, according to the present invention, said upper-directed digital image signal is merged by vicinity pixels, and detection is made upon the defects upon basis of said image signal merged, within said signal processing system. And, also according to the present invention, said signal processing system further comprises a classifying means for classifying said defects detected into different categories. Further, according to the present invention, said signal processing system has a classifying means for classifying the category of the defects, from the each digital image signal, which is converted in said A/D converter. And further, according to the present invention, said signal processing system further comprises a classifying means for classifying said defects detected into different categories. Also, according to the present invention, said signal processing system further comprises a size measuring means for measuring sizes of said defects detected.

Also, according to the present invention, the defects inspecting apparatus, as described in the above, further comprising an optical microscope for observing an optical image upon said inspection target. And, according to the present invention, an area or a mark indicative of coordinates of the defects detected by said signal processing system upon a screen observed on said optical microscope.

Also, according to the present invention, said illumination light beam is exchangeable between a high-inclination angle and a low-inclination angle with respect to the surface of said inspection target substrate within said illumination optic system; and further comprising: a signal processing system, having a defects detection processing portion for detecting the defects upon basis of the digital image signals, which are converted within said A/D converter portion when illumination is made at the high-inclination angle and at the low-inclination angle within said illumination optic system, a characteristic-quantity calculator portion for calculating characteristic quantities, about the defects detected from said defects detection processor portion, and an integration processor portion for obtaining the characteristic quantities about the defects, on which coincidence can be considered between the defects detected from said defects detection processor portion when the illumination is made at the high-inclination angle and the defects detected from said defects detection processor portion when the illumination is made at the low-inclination angle, and for classifying the category of the defects upon basis of said characteristic quantities obtained.

Also, according to the present invention, for accomplishing the above-mentioned objects, there is further provided a defects inspecting apparatus, comprising: a scanning stage for running into a predetermined direction while mounting an inspection target substrate thereon; an illumination optic system for irradiating an illumination spot upon a surface of said inspection target substrate, scanning it into a direction perpendicular to the running direction of said scanning stage; a detecting optic system, having an image-forming optic system for condensing reflected/scattered lights, which are generated from said inspection target substrate due to scanning of the illumination spot irradiated within said illumination optic system, and for forming an image thereof, plural numbers of optical fibers receiving lights of the image of reflected/scattered lights, which is formed said image-forming optic system due to scanning of the illumination spot, and thereby for guiding, and photomultiplier tubes receiving an optical image due to the scanning of the illumination spot, guided by said plural numbers of optical fibers, and for converting it into a signal; and a signal processing system for converting the signal obtained from each of said photomultiplier tubes into a digital signal, and for detecting defects upon basis of said digital signal converted.

Also, according to the present invention, for accomplishing the objects mentioned above, there is further provided a defects inspecting apparatus, comprising: a scanning stage for running into a predetermined direction while mounting an inspection target substrate thereon; an illumination optic system, having plural numbers of optical modulators for modulating each of plural number of illumination light beams by frequencies, differing from each other, an optical deflector for deflecting the plural numbers of illumination light beams, which are modulate through said plural numbers of optical modulators, into a direction about normal to the running direction of said scanning stage, and a condenser optic system for condensing the plural numbers of illumination light beams, which are deflected by said deflector, upon a surface of said inspection target substrate in a form of plural numbers of illumination spots, thereby for irradiating; a detecting optic system, having an image-forming optic system for condensing reflected/scattered lights, which are generated from said inspection target substrate due to scanning of the plural numbers of illumination spot irradiated within said illumination optic system, and for forming an image thereof, a photo-detector for receiving lights of the image of reflected/scattered lights, which is formed said image-forming optic system due to scanning of the plural numbers of illumination spots, and for converting it into a signal; and a signal processing system, having plural numbers of synchronization detection circuits for extracting components corresponding to frequencies, each being modulated in each of said optical modulators, from the signal converted within the photo-detector of said detection optic system, and for detecting defects upon basis of signals extracted from said plural numbers of synchronization detection circuits, as well as, a method thereof.

Also, according to the present invention, said photo-detector comprises optical fibers for guiding the image of reflected/scattered lights due to the scanning of the plural numbers of illumination spots received thereupon, and photomultiplier tubes, receiving the optical image due to the scanning of the plural numbers of illumination spots, which are guided through said optical fibers, and for converting it into a signal.

And, further, according to the present invention, for accomplishing the objects mentioned above, there is provided a defects inspecting method, comprising the followings steps of: a first step for irradiating an illumination light beam upon a surface of an inspection target substrate, having circuit patterns thereon, by an illumination optic system, condensing reflected/scattered lights generated from said inspection target substrate irradiated through an objection lens, so as to form an image thereof through an image-forming system, receiving the reflected/scattered lights upon an upper-directed photo-detector, so as to convert into a first image signal, and thereby detecting defects lying on the surface of said inspection target, having the circuit patters thereon, upon basis of said first digital image signal converted; and a second step for irradiating illumination light beam upon a surface of a transparent film on the inspection target substrate through said illumination optic system at a predetermined inclination angle thereto, condensing reflected/scattered lights generated from said inspection target substrate irradiated from a direction inclined so that it flatly intersect said illumination direction, by means of the image-forming optic system so as to form an image thereof, receiving said reflected/scattered lights forming the image thereof upon a photo-detector, so as to convert it into a second image signal, and thereby detecting defects lying on the surface of the transparent film on said inspection target substrate upon basis of said second digital image signal converted.

As was explained in the above, according to the present invention, it is possible to obtain an effect of enabling an inspection about the defects, such as, fine or microscopic foreign matters and/or scratches, etc., of 0.1 µm on a level thereof, upon an inspection target substrate, on the surface of which a transparent film is formed, and/or an inspection target substrate, on which repetitive patterns and non-repetitive patterns are mixed with, at high sensitivity and also at high speed.

And, according to the present invention, it is also possible to obtain an effect of enabling an inspection about, not only the defects, such as, foreign matters and/or scratches or the like, of 0.1 µm on a level thereof, but also defects, such as, caused due to foreign matters short-circuiting between wiring patterns, and/or the film-like foreign matters, in particular, upon the inspection target substrate, on which repetitive patterns and non-repetitive patterns are mixed with, at high sensitivity and also at high speed.

Further, according to the present invention, it is also possible to obtain an effect of enabling classification of the defects, such as, foreign matters, etc., which are detected, and also measurement on sizes thereof.

BRIEF DESCRIPTION OF THE SEVERAL VIEWS OF THE DRAWING

Those and other objects, features and advantages of the present invention will become more readily apparent from the following detailed description, when taken in conjunction with the accompanying drawings wherein:

FIGS. 19(a) and 19(b) are views for explaining a method of measuring size of the defects, including the foreign matters, etc., for example;

FIG. 20 is a view for explaining about other embodiment, in particular, relating to the method for calculating out an amount of the scattered lights from the defects, including the foreign matters, etc., for example;

FIGS. 22(a) and 22(b) show classification graphs to be used in the classification of defects, including the foreign matters, etc., for example;

BEST EMBODIMENT FOR PRACTICING THE INVENTION

Hereinafter, embodiments according to the present invention will be fully explained, by referring to the attached drawings.

A defects inspecting apparatus, according to the present invention, enables to make an inspection about various kinds of defects, such as, foreign matters, pattern defects and/or micro-scratches, etc., for example, on a substrate to be inspected, including, a wafer or the like, of various kinds of products and on various kinds of manufacturing processes thereof, further including fine ones and large ones, at high sensitivity and at high speed. For such purposes, within the defects inspection apparatus according to the present invention, as is shown in FIG. 1, it is characterized that an irradiation angle α of a slit-like beam 201, which is irradiated by an illumination optic system 10, is made variable depending on an object to be inspected (i.e., an inspection target), and also that the magnifying power of a detection optic system 200 is made variable, while disposing the detection optic system 200 so that the surface of the inspection target and the light-receiving surface of a detector 26 are in a relationship of image-forming; thereby, fitting a size of detecting pixel to that of the defects to be inspected.

Further, the defects inspecting apparatus, according to the present invention, has also a function of classifying the defects upon basis of the difference between scattered lights, which can be obtained from the defects, through different irradiation angles of the illumination lights, in the form of characteristic amounts or quantities, for example.

Next, explanation will be given about the details of an embodiment of the defects inspecting apparatus, according to the present invention. In the embodiment mentioned below, although explanation will be given about, in particular, in a case when it is applied into an inspection of small/large foreign matters and/or pattern defects and/or micro-scratches, etc., on a semiconductor wafer; however, it can be also applied onto a photo-mask, a TFT (Thin Film Transistor), PDP (Plasma Display Panel), etc., but should not be limited only to the semiconductor wafer.

Figure 1:
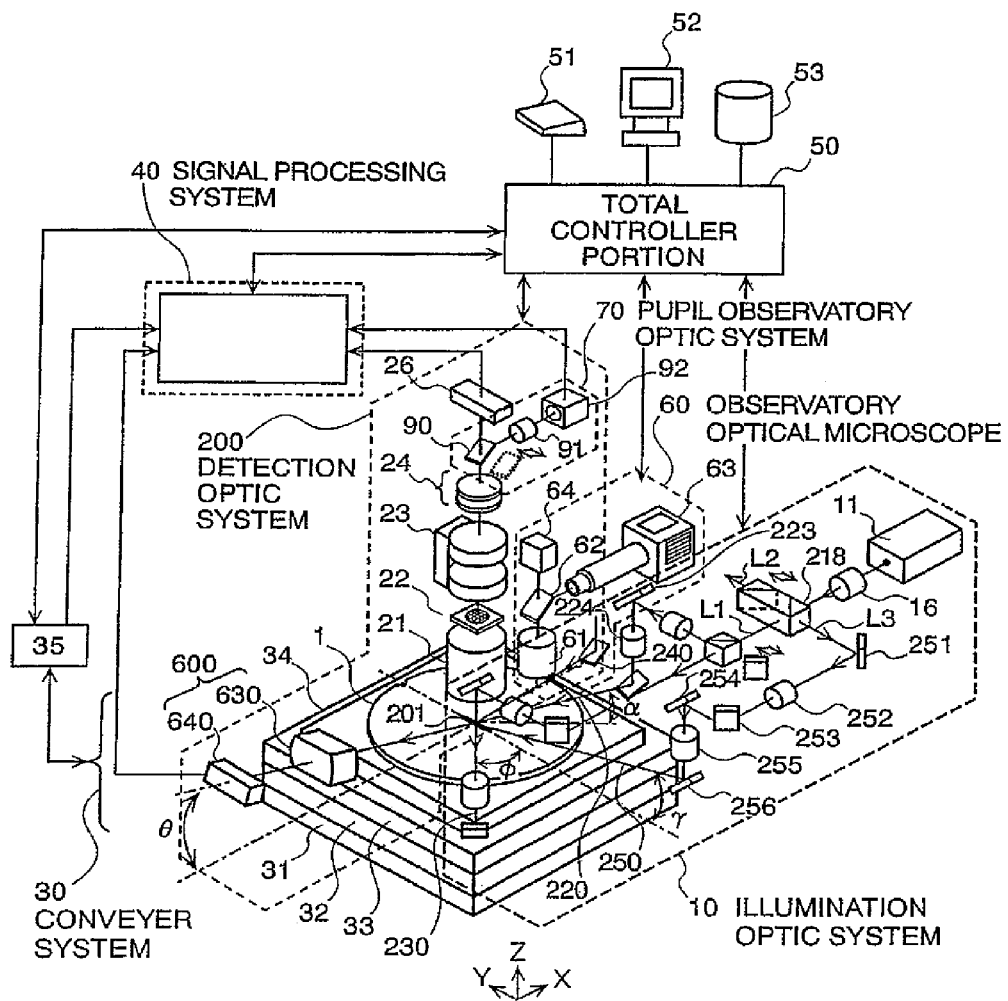
FIG. 1 is a brief structure view for showing an embodiment of the defects inspecting apparatus, according to the present invention.
Figure 7A:
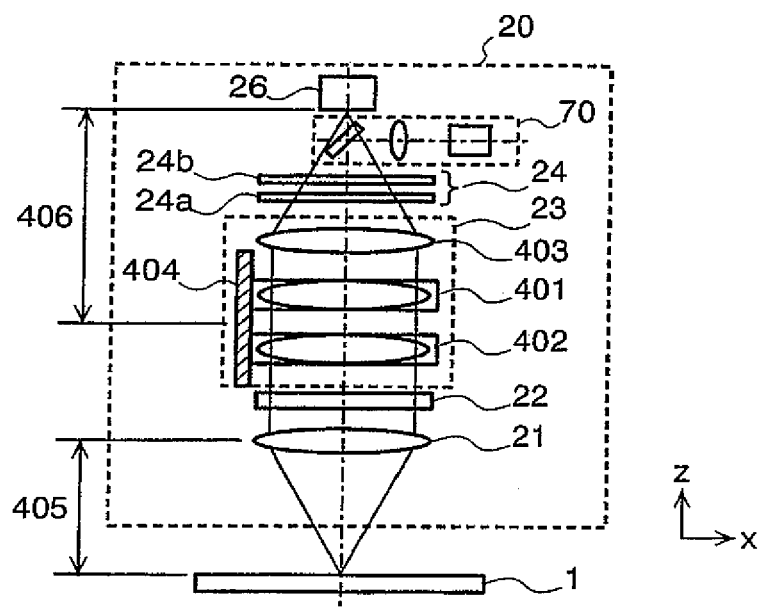
FIGS. 7(a) and 7(b) are views for explaining about the variable operation of an optic system, being variable in magnification power thereof, which is shown in FIG. 1.

By the way, the defects inspecting apparatus, according to the present invention, comprises: a conveyer system 30, having X, Y and Z stages 31, 32, 33, and 34 for mounting thereon and moving a substrate 1, i.e., an inspection target, such as, a wafer or the like, which can be obtained from various kinds of products and/or various kinds of manufacturing processes, and a controller 35, as is shown in FIG. 1; an illumination optic system 10 for making illumination upon the substrate 1, i.e., the inspection target, from plural oblique directions through lenses, mirrors, etc., after expanding a light beam emitted from a laser-light source 11 up to a certain size through a beam enlarging optic system 16; a detection optic system 200, being constructed with an objection lens 21, a space filter 22, an image-forming optic system 23, a group of optic filters 24 (which will be shown in FIG. 7(a)), and a photo-detector 26, such as, of TDI image sensors or the like, for example, and further having a magnification-variable detection optic system 20 for detecting reflected/diffracted lights (or, scattered light) reflected and/or diffracted from a region where illumination is made by the illumination optic system 10, as well as, a side-directed detection optic system 600 having an image-forming optic system 630 and a photo-detector 640, etc.; a signal processing system 40; and a total controller portion 50 for setting up inspection conditions and for controlling the illumination optic system 10, the detection optic system 200 including the magnification-variable detection optic system 20, etc., the conveyer system 30, the signal processing system 40, an observatory optic system 60, and so on. The total controller portion 50 is equipped with an input/output means 51 (including a keyboard and/or a network, too), a display means 52, and a memory portion 53.

Further, this inspecting apparatus of foreign matters is provided with an automatic focus controller system (not shown in figures), so that a surface image of the wafer can be formed upon light-receiving surfaces of the photo-detectors 26 and 640.

[Illumination Optic System 10]

Figure 2A:
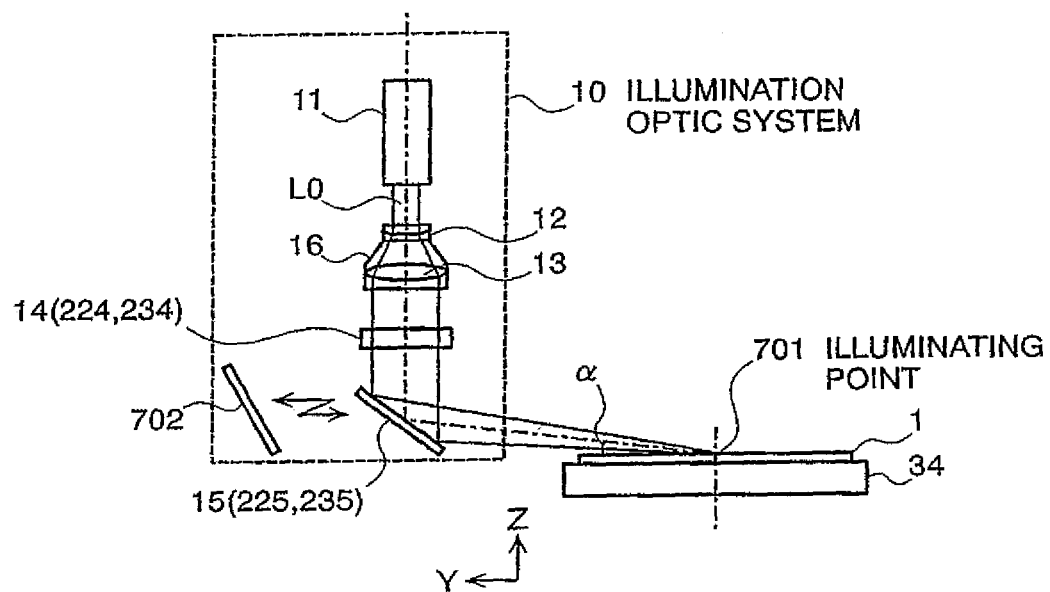
FIGS. 2(*a*) and 2(*b*) are views for showing an illumination optic system shown in FIG. 1; in particular, FIG. 2(*a*) is a front view thereof and FIG. 2(*b*) a perspective view for showing the illumination optic system, as a whole.
Figure 2B:
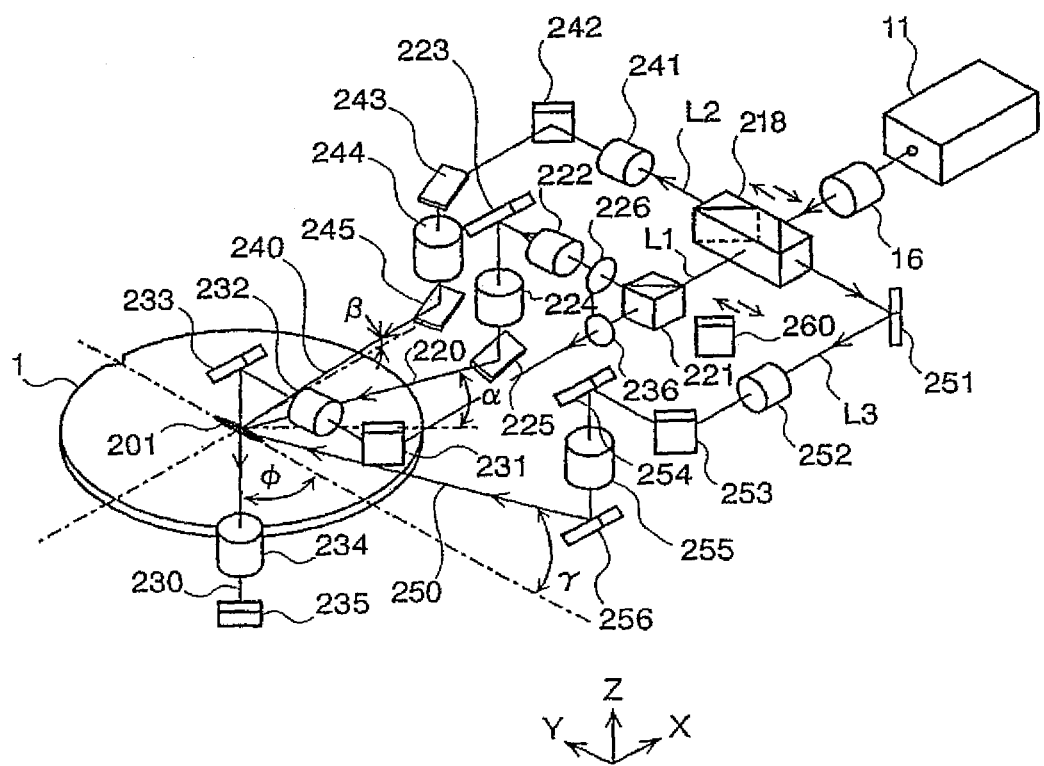
Figure 3:
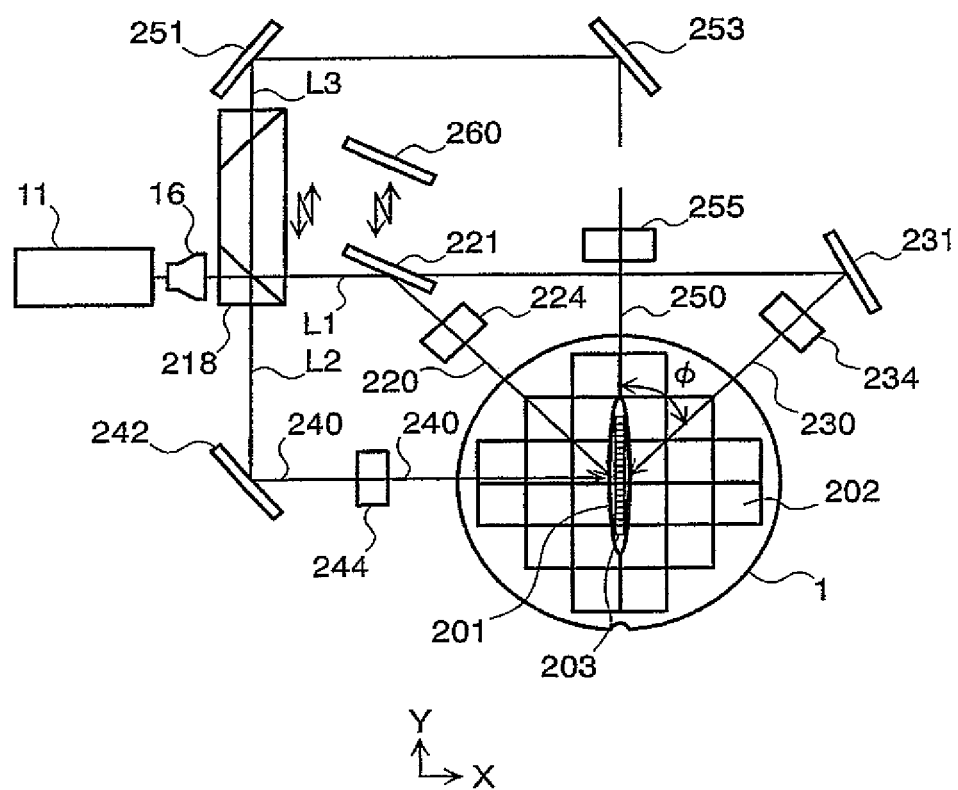
FIG. 3 is a plan view for showing the entire of illumination optic system, which is shown in FIG. 1.

The present inspecting apparatus is so configured in the structure, that illumination can be made upon the surface of the substrate 1, i.e., the inspection target, from plural numbers of directions. Within the structure of this illumination optic system 10, the light L0 emitted from the laser-light source is irradiated upon the wafer (i.e., the inspection target substrate) mounted on the sample-mounting base 34, from one (1) or more directions (for example, four (4) directions in FIG. 3), flatly, in the form of a slit-like beam 201, through the beam enlarging optic system 16, which is constructed with a concave lens 12 and a convex lens 13, etc., a conical surface lens 14 for forming the slit-like light beam, and a mirror 15, as is shown in FIGS. 2(a) and 2(b). It is also configured such that, in this instance, a longitudinal direction of the slit-like beam 201 is directed into the direction of the alignment of chips. The reason of forming the illumination light into the slit-like beam 201 lies in that light-receiving elements aligned can collectively detect the scattered lights from the foreign matters and/or the defects, once, which are generated due to the illumination, and thereby achieving high speed of inspection. Namely, as is shown in FIG. 3, the slit-like beam 201, being irradiated upon the wafer 1, on which the chips are aligned directing into the scanning directions of the X stage 31 and the Y stage 32, has a shape of being narrow in the scanning direction X of the X stage 31, but wide in the Y direction perpendicular to that (i.e., the scanning direction of the Y stage 32). And, this slit-like beam 201 is irradiated, so that an image of the light source can be formed in the X direction while it comes to be parallel light in the Y direction, due to the provision of, such as, a cylindrical lens within an optical path. However, the details of this illumination directing into three (3) directions is described in Japanese Patent Laying-Open No. 2000-105203, for example.

By the way, the reason of directing the longitudinal direction of the slit-like beam 201 into the aligning direction of chips, with respect to the wafer 1, lies in that comparison can be made, easily, between the chips on an image signal, while keeping pixel alignments of the photo-detector 26 and moving direction of the X stage 31 in parallel with, and also that calculation can be made easily, about the positional coordinates of the foreign matters; thereby, as a result, achieving an effect of enabling the inspection of the foreign matters at high speed.

Figure 4A:
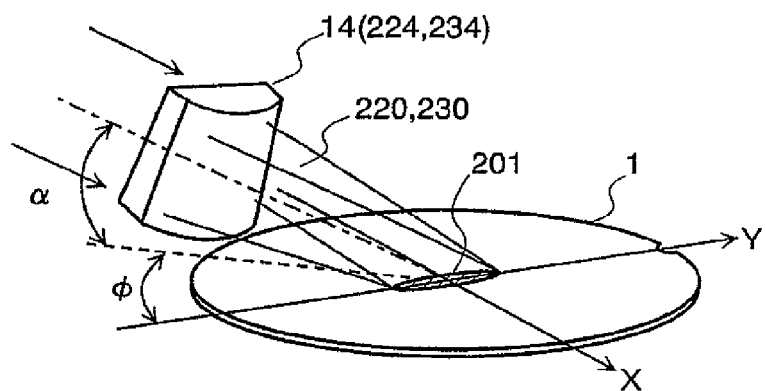
FIGS. 4(*a*) through 4(*c*) are views for showing a method of irradiating four (4) illumination light beams; in particular, FIG. 4(*a*) shows the illumination method, with using a lens having a conical curved surface, and FIGS. 3(*b*) and 3(*c*) the illumination with using a cylindrical lens therein.

In particular, the conical surface lens 14 (224, 234) is necessary for directing the illumination of the slit-like beam 201 of illumination light beams 220 and 230, which are irradiated from the direction inclined by φ with respect to the Y direction, in the plane surface thereof, into the direction of alignment of the chips 202 on the wafer 1, and also for forming it to be orthogonal to the scanning direction X of the X stage 31. This conical surface lens 14 (224, 234) is a lens, being different in the focal distances at positions on the longitudinal direction thereof, and changing the focal distances, linearly; i.e., the radius of curvature is continuously changed in the longitudinal direction thereof. With such structure thereof, if irradiating from an oblique direction (satisfying an inclination of both, an angle α and a direction φ), as is shown in FIG. 4(a), an illumination can be obtained by the slit-like beam 201, which is reduced in the X direction and is collimated in the Y direction thereof. Further, it has such the structure that an illumination angle α can be changed depending upon kinds of the foreign matters and/or defects, for example, as being the inspection target on the substrate 1 to be inspected, by exchanging the mirror 15 (225, 235) and also a mirror 702, mechanically, as shown in FIG. 2(a), or by changing an angle of one (1) piece of the mirror 15 upon basis of an instruction from the total controller portion 50 with an aid of a rotation means not shown in figures. In FIG. 2(a), the laser illumination is irradiated at an illumination point or position 701 by means of the mirror 15. In case of changing the illumination angle α, it is enough to replace the mirror 15 with the mirror 702, which is different from the mirror 15 in the angle thereof, and further move that mirror 702 for irradiating the laser light at the illumination point 701 into the Z direction. In this instance, since the distance is changed from the convex lens 13 up to the illumination point 701, then there is necessity of changing the position of the convex lens 13 and/or changing it to a convex lens having different focal distance.

Figure 4B:
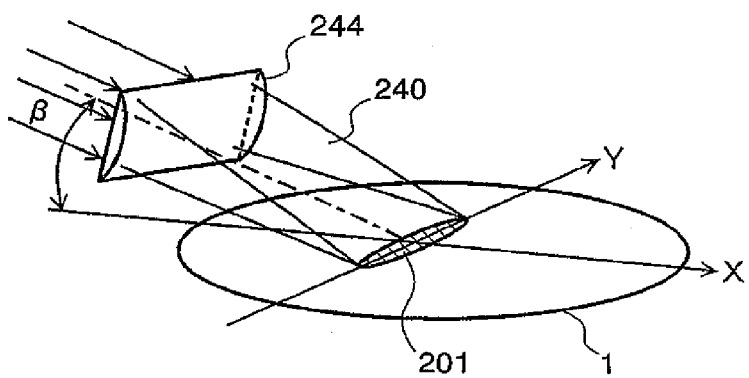
Figure 4C:
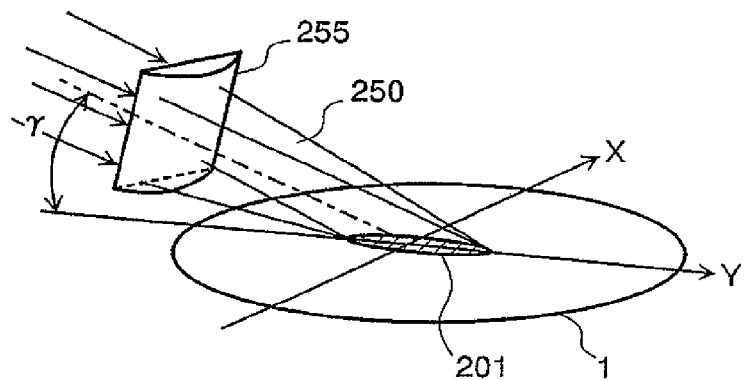

Further, upon illumination made from the X direction and the Y direction, as is shown in FIGS. 4(b) and 4(c), it is possible to form the slit-like beam 201 by means of cylindrical lenses 244 and 255.

As was explained in the above, the construction is so made, that the slit-like beam 201 has an illumination area or region of covering over pixel alignments 203 of the photo-detectors 26 and 640, in any case of the illumination angles, and that the slit-like beam 201 is coincident with on the wafer, upon illumination irradiated from any direction.

With this, it is possible to obtain an illumination having parallel rays, and also at the angel in vicinity of φ=45 degree. In particular, converting the slit-like beam 201 into the parallel rays into the Y direction brings about that the diffracted light patterns generated from circuit patterns is blocked or shielded by means of the space filter 22.

However, since description is given about the method for manufacturing the conical surface lens 14, in Japanese Patent Laying-Open No. 2000-10520 (2000), for example; therefore, it will be omitted herein.

Next, explanation will be made about an embodiment of changing the illumination angle α and the illumination direction φ of the illumination optic system 10 depending upon the substrate, as the inspection target, which is mounted on the stage, upon basis of an instruction from the total controller portion 50. By the way, the reason of forming the slit-like beam 201 on the wafer 1 by plural numbers of the illumination angles is for dealing with the detections of various types of foreign matters and/or defects, which are generated on the surface of the wafer 1. Thus, detection is targeted upon the pattern defects and/or foreign matters having a low height. Since the illumination angle α increases in an amount of reflected/diffracted lights from the circuit patterns when it comes up to high angle, thereby lowering the S/N ratio, therefore an optimal value should be applied, which can be obtained experimentally. As an example, if trying to detect mainly the foreign matters having low height on the surface of wafer, it is preferable that the illumination angle α be set to be small, such as, from 1 degree up to 5 degree, for example. By setting the illumination angle α to be small, in this manner, the S/N ratio can be improved of the foreign matters upon the most surface of the wafer. Also, when trying to detect mainly the foreign matters between wiring patterns and/or the pattern defects, during the wiring process, it is preferable to set the illumination angle large; however, from a viewpoint of a relationship of the S/N ratio between the circuit patterns and the foreign matters, it is desirable to be set from 45 degree to 55 degree, approximately. Also, if there is correspondence between the manufacturing processes (such as, an etching process and a CMP process, for example) of the inspection target and the foreign matters and/or the defects to be detected, it is also possible to determine on which illumination should be set up, in advance, within an inspection recipe. Further, for detecting the foreign matters and the pattern defects on the wafer surface mentioned above, it is also possible to set up the illumination angle at a value defined between those angles mentioned above.

Figure 5:
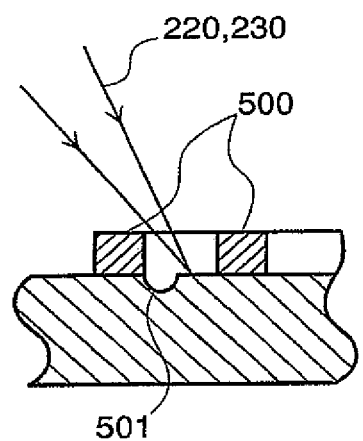
FIG. 5 is a view for explaining about a condition where it is difficult to detect the defects lying between wiring patterns, in particular, when irradiating the illumination light beams 220 and 230 thereupon.

Further, regarding the illumination direction φ, in case of the wiring process, for example, when the illumination light beams 220 and 230 are irradiated from the direction in vicinity of 45 degree of φ, since there may be generated a situation where no scattering light diffracted can be obtained from the foreign matters and/or the defects 501 lying between the wiring patters 500, as is shown in FIG. 5, therefore, it is preferable to select the illumination 240 from the directions in parallel with the aligning direction of patterns of an illumination circuit (for example, X direction). In other words, fitting the parallel direction of the illumination light 240 to the direction of wiring patterns 500 enables easy detection of the foreign matters and/or defects between the wiring patterns 500. Also, in a case if the circuit patterns on the wafer 1 include a contact hole or a capacitor, etc., other than the wiring patterns, since there is no specific directional property (or, orientation), it is preferable that the illumination light beams 220 and 230 are irradiated onto the chip from a direction of φ in vicinity of 45 degree.

Further, detailed description will be made about the illumination optic system 10.

First, explanation will be made on a method of changing the illumination direction φ. FIG. 2(b) and FIG. 3 are plane views; in particular, in the case where four (4) sets of the illumination optic systems 10 are constructed by using only one (1) lager light-source 11. A branching optical element 218, being built up with a mirror, a prism, and so on, transmits the laser light L0 emitted from the laser light-source therethrough, or reflects it thereupon, thereby to guide it into three (3) directions, through movement in the position thereof in the Y direction. A first laser light L1 penetrating through the branching optical element 218 is separated into a penetrating light and a reflected light through a branching optical element 221, such as, a half prism or the like (for example, a polarization beam splitter), wherein from the light penetrating therethrough can be obtained the illumination light beam 230, having the inclination angle of α and the direction inclined by φ from the Y axis, by reflecting it upon the mirror 235, again, via a mirror 231, an optic system 232 for adjusting the beam diameter, a mirror 233 and the conical surface lens 234 shown in FIG. 4(a), while from the light reflected upon the other branching optical system 221 can be obtained the illumination light beam 220, having the inclination angle of α and the direction inclined by φ from the Y axis, by reflecting it upon the mirror 225, again, via an optic system 222 for adjusting the beam diameter, a mirror 223 and the conical surface lens 224 shown in FIG. 4(a). However, the beam-diameter adjusting optical systems 222 and 232 are provided for adjusting the beam diameters of the laser beams, which are incident upon the conical surface lenses 224 and 234, so that the slit-like beam 201 can be obtained being equal in the size, which is irradiated upon the wafer 1. Also with provision of a mirror 260 in the place of the half-prism, as being the branching optic element 221, it is possible to obtain an illumination from one side. Also, with insertion of wave plates (e.g., λ/2 plates) 226 and 236 behind the branching optic element (for example, the polarization beam splitter) 221, it enables to align the polarization direction of the laser lights to be irradiated thereupon.

By the way, after passing through the beam-diameter adjusting optical element 241, the second laser light L2 reflected upon the branching optical system 218 is further reflected upon mirrors 242 and 243, to be incident upon the cylindrical lens 244, as is shown in FIG. 4(b), and it can be obtained in the form of the illumination light beam 240, having an angle β inclined from the X direction, through reflection thereof upon a mirror 245; and, the third laser light L3 reflected upon the branching optical system 218 is further reflected upon mirrors 251, 253 and 254, to be incident upon the cylindrical lens 255, as is shown in FIG. 4(c), and it can be obtained in the form of the illumination light beam 250, having an angle γ inclined from the Y direction, through reflection thereof upon a mirror 256. With the illumination light beam 240 mentioned above, for example, in the wiring process, it is possible to fit the direction of illumination (i.e., the X direction) thereto, in particular, in the case where the wiring patters formed on the wafer are parallel to the X and Y directions in a large number thereof, thereby enabling an easy detection of the foreign matters and defects 501 lying between the wiring patterns 500, as shown in FIG. 5. For the wiring patterns aligning into the Y direction, it is enough to rotate the wafer 1 around, by an angle of 90 degree. And, with the inclination angle β of the illumination light beam 240, it may be set at the middle angle or the high angle mentioned above, from a viewpoint of detection of the foreign matters and/or defects lying between the wiring patters. It is also possible to make the inclination angle β exchangeable, in the similar manner to the angle α. In this manner, it is possible to make the mirror 245 small in sizes thereof, from the fact that the illumination light can be focused to be narrow in the X direction by means of the cylindrical lens 244, when it is irradiated from the X direction, and as a result thereof, it is also possible to obtain the illumination at the angle, even being high, by putting that mirror 245 into between around the object lens 21 and the wafer 1.

Figure 6:
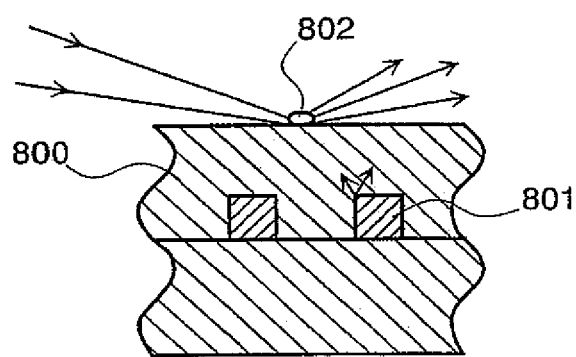
FIG. 6 is a view for explaining about a condition where scattered lights are generated, in particular, when irradiating an oblique illumination light beam 250 upon a transparent film.

In particular, according to the present invention, as will be mentioned later by referring to FIG. 6, the illumination is made at the inclination angle γ from the longitudinal direction (i.e., the Y direction) of the slit-like beam 201, by means of the illumination light beam 250 upon basis of the third laser beam L3, as was mentioned above, so as to detect fine or microscopic foreign matters and/or scratches on a transparent film (such as, an oxidation file) 800, upon which the CMP (Chemical Mechanical Polishing) process is treated, from an oblique direction co intersecting the Y direction, so as to lesson receiving of the ill influences due to the lights scattered from background patterns 801. With this inclination angle γ of the illumination light beam 250, it is preferable to be set from 5 degree to 10 degree, approximately, at an angle relatively low, from a viewpoint of detection of the fine foreign matters and/or scratches or the like, on the oxidation film 800. By the way, when using a cylindrical lens 255 having a uniform focal distance therein, the slit-like beam 201 comes to be drum-like, being narrowed in width at a center thereof. However, it is possible to obtain the slit-like beam, not being narrowed at the center, by exchanging the focal distances of the cylindrical lens 255, so as to be fit to the inclination angle γ.

Herein, when trying to obtain an illumination only from the illumination light beam 240, it can be achieved by exchanging the mirror portion within the branching optical element 218. Also, when trying to obtain the illuminating from two (2) directions by means of the illumination light beams 220 and 230, it can be achieved through taking out the branching optical system 218, or replacing it by a transmitting portion.

Further, as the laser light-source 11, it is desirable to apply the second high-frequency SHG of YAG laser of a high output, having a wavelength 532 nm, for example, by taking the facts into the consideration, that it enables the inspection with high sensitivity and that it is cheap in the maintenance cost; however, there is not always a necessity that the wavelength of 532 nm, but it may also be a light source, such as, a UV (ultraviolet) laser, a far ultraviolet (FUV) laser, a vacuum UV (ultraviolet) laser, an Ar laser, a nitrogen laser, a He—Cd laser, an excimer laser, or a semiconductor laser, etc. As an advantage of applying each of those lasers, if the laser wavelength is shortened, since the resolution of an image detected can be increased, therefore it is possible to achieve the inspection thereof with high sensitivity. However, if applying the wavelength of about 0.34 μm, then the NA of the objection lens 21 be 0.4 or more or less, or if applying the wavelength of about 0.17 μm, then the NA of the objection lens 21 comes to be 0.2 or more or less; thereby enabling an improvement upon the detection sensitivity since the much of diffracted lights can be incident upon the objection lens 21. Also, with applying of the semiconductor laser or the like, there can be obtained an apparatus small-sized and of low-costs.

[Detection Optic System 200]

Figure 7B:
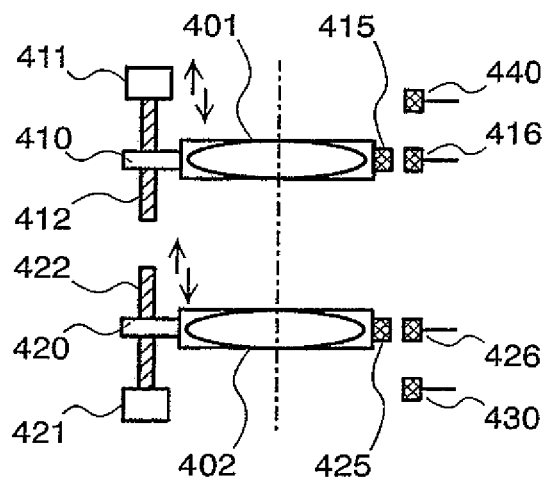
Figure 8A:
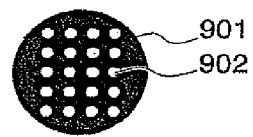
FIGS. 8(a) to 8(c) are views for explaining about automatic setting of shading patterns within a space filter.
Figure 8B:
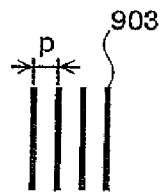
Figure 8C:
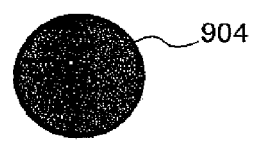

Firstly, explanation will be given about the magnification-variable detection optic system (an upper-directed detection optic system) 20 of the detection optic system 200, by referring to FIGS. 1, 7 and FIG. 8. The magnification-variable detection optic system (the upper-directed detection optic system) 20 is constructed in such that, the lights reflected and/or diffracted from the inspection target substrate 1, such as, the wafer, etc., can be detected upon the photo-detector 26, such as, the TDI image sensors or the like, through the objection lens 21, the space filter 22, the image-forming optic system (a magnification-variable image-forming optic system) 23, and the optic filter group 24 having a ND filter 24*a* and a polarization plate 24*b*, etc.

The space filter 22 has a function of passing the scattered lights therethrough, which are generated from the foreign matters, while shielding the lights of a Fourier conversion image due to the lights reflected and/or diffracted from the repetitive patterns on the wafer 1, and it is disposed within a space frequency area of the objection lens 21, i.e., an image-forming point of the Fourier conversion (corresponding to an exit pupil).

Next, explanation will be made about an automatic setting of the space filter 22 of using a pupil observatory optic system 70, by referring to FIG. 1 and FIGS. 8(*a*)-8(*c*). Namely, the space filter 22 is so adjusted that it picks up an image, for example, of the lights reflected and/or diffracted from the repetitive diffraction patterns 902 at the position where the image of Fourier conversion is formed, as is shown in FIG. 8(*a*), by means of the pupil observatory optic system 70 including a mirror 90, which can be escaped from during the inspection operation, a projection lens 91, a TV camera 92, on the optical path of the detection optic system 200, and it obtains an image 904 having no bright spot of the lights reflected and/or diffracted from the circuit patterns at the image-forming position of the Fourier conversion, as is shown in FIG. 8(*c*), by changing an interval or pitch "p" of a light shielding portion 903, which is provided at the position where the Fourier conversion can be formed, through a mechanism not shown figures, as is described in Japanese Patent Laying-Open No. Hei 5-218163 (1993), for example. Those are automatically set up through adjustment on the pitch "p" and/or rotation direction of the light shielding portion 903 within the space filter 22, upon basis of an instruction from the total controller portion 50 processing the signals from the TV camera 92 within the signal processing system 40. However, without applying such the light shielding plate therein, as was mentioned above, but it may be made through forming a light shielding portion reduced in sizes, such as, through forming whites and blacks in reverse on a transparent substrate upon basis of the signals from the TV camera 92.

The present inspecting apparatus has such a function of conducting the defect inspection at a high speed, and also of conducting the inspection with high sensitivity, but at a low-speed. Namely, the inspection can be executed with high sensitivity upon an inspection target or an area where the circuit patters are manufactured at high density, since an image signal of high resolution can be obtained with increasing up the magnification of the detection optic system. Also, the high-speed inspection can be achieved by lowering the magnification down, upon an inspection target or an area where the circuit patters are manufactured at low density, while keeping the high sensitivity. With this, it is possible to optimize the sizes of the foreign matters to be detected, as well as, the size of the detecting pixels; thereby bringing about an effect of eliminating noises other than those from the foreign matters, so as to detect only the lights scattered from the foreign matters, with high efficiency. Namely, with the present inspection apparatus, the magnification of the detection optic system 200 provided above the wafer 1 can be changed with simple structure thereof.

Next, explanation will be made about the operation of changing the magnification of the detection optic system 200, by referring to FIGS. 7(*a*)-7(*b*). Change of the magnification of the detection optic system 200 is executed upon basis of an instruction from the total controller portion 50. The image-forming optic system (i.e., the magnification-variable image-forming optic system) 23 comprises a movable lenses 401 and 402, a fixed lens 403, and a moving mechanism 404, and is characterized in that the magnification of a wafer surface formed on the photo-detector 26 can be changed, but without changing the positions of the objection lens 21 and the space filter 22 when changing the magnification thereof. Namely, it has the following advantages: even when changing the magnification, but there is no necessity of changing the relative position between the inspection target substrate 1 and the photo-detector 26, when changing the magnification; the magnification can be changed with the simple structure of a driving or moving mechanism 404 when changing the magnification; and further, there is no necessity of changing the space filter, since no change is caused on sizes of the Fourier conversion surface.

The magnification M of the magnification-variable detection optic system 20 can be calculated out from the equation (1), which will be shown below, while assuming that the focal distance 405 of the objection lens 21 is $f_1$ and the focal distance 406 of the image-forming optic system 23 $f_2$, respectively:

$$M = f_2/f_1 \tag{1}$$

Accordingly, for building up the magnification-variable detection optic system 20 to be M in the magnification thereof, since $f_1$ has a fixed value, therefore $f_2$ is moved to the position where (M/$f_1$) can be satisfied.

Next, explanation will be given in details of the moving mechanism 404, by referring to FIG. 7(b). This FIG. 7(b) shows the structure for positioning the movable lenses 401 and 402 at specific positions thereof, within the moving mechanism 404. However, the moving mechanism 404 is also applicable to make a control of positioning of those movable lenses 401 and 402 at arbitrary positions. Also, the moving mechanism 404 is constructed with lens holder portions 410 and 420 for the movable lenses 401 and 402, ball screws 412 and 422, and also motors 411 and 421. Thus, the movable lens 401, which is held by the lens holder portion 410, and also the lens holder portion 410 move through rotation of the ball screw 412 driven by means of the motor 411, while the movable lens 402, which is held by the lens holder 420, moves through rotation of the ball screw 422 driven by means of the motor 421, independently, to predetermined positions in the Z direction, respectively.

And, providing the movable portion 415 or 425 on the positioning sensor at an end of the lens holder portion 410 or 420, which holds the movable lens 401 or 402, while providing a detector portion 416 or 426 of the positing sensor at a stopping position of the movable lens 410 or 420, the motor 411 or 421 is driven, so as to move the lens holder portion into the Z direction, then the each positioning sensor 416 or 426, being provided at a position of the desired magnification, detects the movable portion of the positioning sensor, and thereby achieving the positioning thereof. However, the positioning sensor 440 is a limit sensor for an upper limit in the Z direction, while the positioning sensor 430 a limit sensor for a lower limit in the Z direction. Herein, as such the positioning sensor mentioned above, there can be considered an optical or a magnetic sensor to be applied thereto.

Although those operations are conducted upon basis of the instruction from the total controller portion 50, but the magnification should be set at, depending upon the pattern density on the inspection target substrate 1, which is mounted on the stages 31-34. For example, when the circuit pattern has a high density, the high magnification should be selected, to obtain an inspection mode of high sensitivity, but when the circuit pattern has a low density or there is necessity of a high-speed inspection, then a low magnification should be selected.

Also, as other embodiment of the magnification-variable detection optic system 20, in particular when change is not frequently made on the magnification, there can be also considered to exchange a unit, by unitizing the portions of the movable lens as a unit. In this instance, there can be obtained a merit of enabling adjustment and maintenance with ease.

Next, explanation will be made on the optical filter group 24. The ND filter 24a is for use of adjusting an amount of lights detected upon the photo-detector 26, and then the photo-detector 26 turns into the saturated state when receiving the reflected lights of high brightness thereupon; therefore, it cannot detect the foreign matters with stability. This ND filter 24a is not always necessary when an amount of irradiation lights can be adjusted within the illumination optic system 10; however, with using the ND filter 24a therein, it is possible to enlarge an adjustable range on an amount of detection lights; thereby enabling an adjustment on the light amount to be the most suitable for various inspection targets. For example, an output can be adjusted from 1 W up to 100 W with using the laser light source 1, and if preparing a filter of 100% penetration and a filter of 1% penetration, as the ND filter 24a, the light amount can be adjusted from 10 mW up to 100 W; therefore, it is possible to adjust the light amount, widely.

The polarization plate 24b is for use of shielding the polarization light components caused due to the lights reflected and/or diffracted from the edges of circuit patterns, and passing a part of the polarization light components therethrough, which are generated from the foreign matters when an illumination is made with polarization lights thereupon, within the illumination optic system 10.

Next, explanation will be given about the photo-detector 26. The photo-detector 26 is an image sensor for receiving the upper-directed lights reflected and/or diffracted, which are condensed by means of the image-forming optic system 23, and for conducting photoelectric conversion thereupon, and it may be a TV camera, a CCD linear sensor, a TDI sensor, an anti-blooming TDI sensor, or a photo-multiplier tube, for example.

Herein, as a manner for selecting the photo-detectors 26 and 640, it is preferable to apply the TV camera or the CCD linear sensor, when building up a cheap inspection apparatus, and it is preferable to apply the sensor having the TDI (Time Delay Integration) function or the photo-multiplier tube, when detecting weak or feeble lights with high sensitivity, such as, when detecting the very fine foreign matters, such as, being less than 0.1 μm, approximately, for example.

Figure 9A:
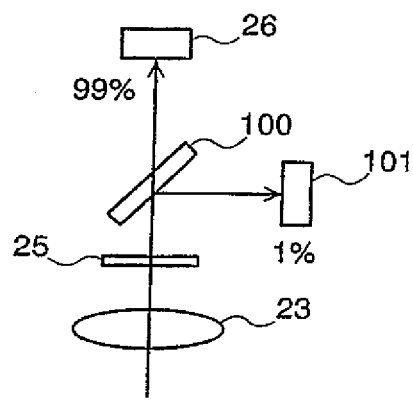
FIGS. 9(a) and 9(b) are views for showing an example, having an optic system of protection from blooming within an upper-directed detection optic system.

Next, explanation will be made about an embodiment for improving dynamic range within the photo-detector. By the way, difference appears in the intensity between the lights reflected and/or diffracted from the circuit patterns, depending upon an inspection target area on the wafer. Thus, comparing between a portion of memory cells, on which the circuit patterns are formed repetitively, and a periphery portion thereof; the intensity is stronger of the lights reflected and/or diffracted from that periphery portion. Also, though it is possible to eliminate the lights reflected and/or diffracted from the circuit patterns of the memory cell portion, much more, by means of the space filter 22, for example; however, it is difficult to eliminate that generated from the periphery portion or the like, since there exist various patterns therein, by means of the space filter 22. Because of being under such the situation, if the dynamic range comes to be large on the lights received upon the photo-detector 26 when the inspection target area reaches to the periphery portion or the like, in other words, in a case when such the lights are incident upon the sensor that it is saturated, it is preferable to apply a sensor added an anti-blooming function thereto; however, as is described, for example, in Japanese Patent Laying-Open No. 2000-105203 (2000), a beam splitter 100, being different in the transmissivity (for example, 99%) and the reflectivity (for example, 1%) thereof, may be disposed at the position of the mirror 90, for example, on the optical path within the detection optic system 20, as is shown in FIG. 9(a), as well as, providing the photo-detectors 26 and 101 on the respective optical paths. Of course, it is also possible to build up the above-mentioned beam splitter 100 with a half-mirror, with provision of the ND filters between that half-mirror and the photo-detectors 26 and 101, separately; thereby, differing an amount of transmitted lights from each other. In this instance, when such strong lights generated from the periphery portion or the like are incident upon the sensor that it is saturated, then the defects, such as, the foreign matters, may be detected upon basis of an image signal, which can be obtained by attenuating or damping an amount of lights received from the photo-detector 101, but with those generated from the memory cell portion, the defects, such as, the foreign matters, may be detected upon basis of the image signal, which can be obtained from the photo-detector 26. However, as a manner for detecting the defects, such as, the foreign matters, upon basis of the image signal (an image signal of enhancing the background, relatively), which can be obtained from the photo-detector 101, there is known a method of extracting a signal indicative of the defects, such as, the foreign matters, etc., which are generated at random, through eliminating the image signal of that background at the level almost same to that by chip comparison in the signal processing. With this, it is possible to detect the defects, such as, the foreign matters, etc., but without conducting the inspection by plural numbers of times, while changing strength of the illumination, in the areas, not only the memory cell portion, but also the periphery portion or the like thereof.

Figure 9B:
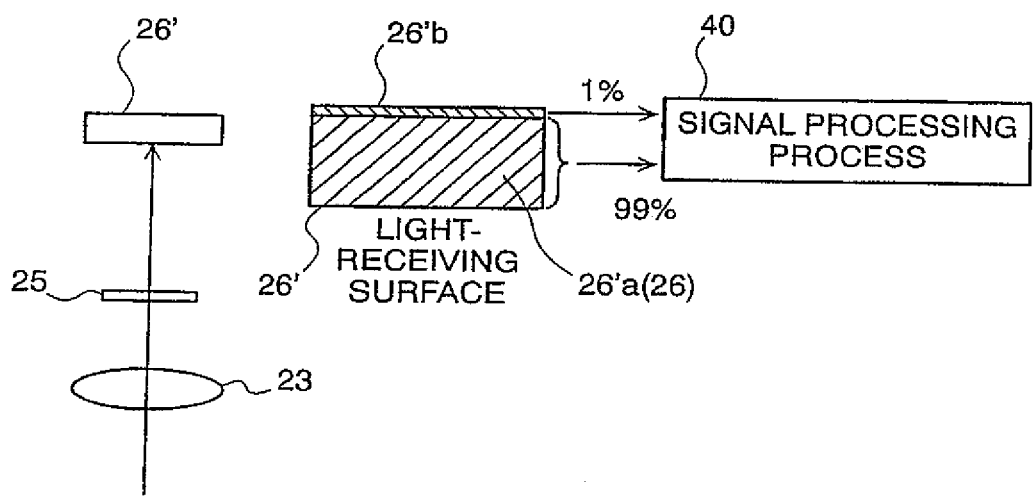

Also, when applying the TDI sensor therein, as is shown in FIG. 9(*b*), there can be considered a case of using an element, on which lines 26'a (26) and 26'b of light receiving portions are formed, being different on stage numbers for taking out signals therefrom, among the lines of light receiving elements of 100 stages, for example, as is shown in FIG. 9(*b*). For example, with the structure of dividing a portion 26'b for taking out an intensity signal of 1% accumulated on the line of light-receiving elements of one (1) stage, and other portion 26'b for taking out an intensity signal of 99% on the lines of light-receiving elements of the remaining 99 stages, the blooming can be prevented from being generated even when strong lights are incident thereon, thereby enabling to process the respective output signals through the signal processing system 40, in the similar to that mentioned above.

Figure 10A:
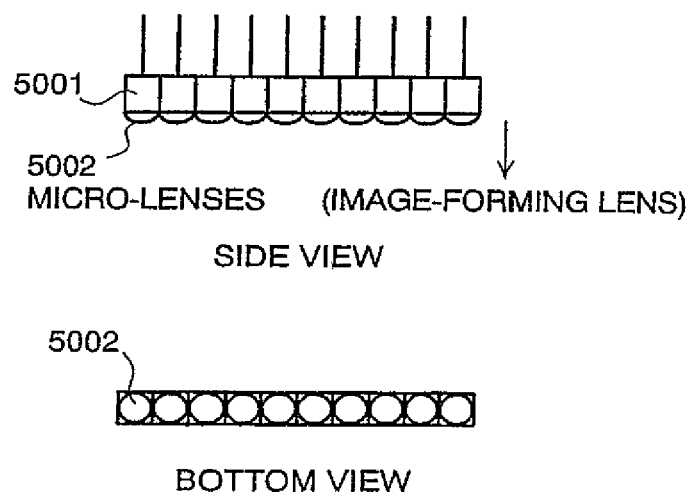
FIGS. 10(a) and 10(b) are views for showing an example of applying photo-multiplier tubes, as a photo-detector.
Figure 10B:
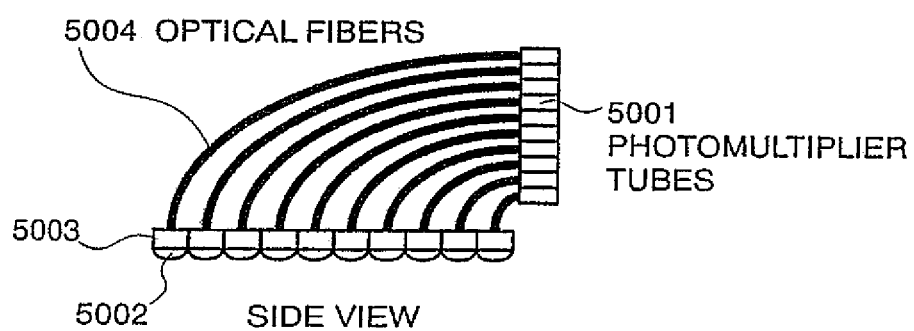

Next, explanation will be made about an embodiment of applying the photo-multiplier tube therein, by referring to FIG. 10. This FIG. 10 shows a sensor of aligning the photo-multiplier tubes in the one-dimensional direction. In this case, since it can be used as a one-dimensional sensor having high sensitivity, therefore it is possible to make an inspection with high sensitivity. With the structure in this instance, as shown in FIG. 10(*a*), micro-lenses 5002 may be attached on a side of the image-forming optic system 23 of the photo-multiplier tubes 5001, thereby detecting the reflected/diffracted lights, which are condensed within the image-forming optic system 23. Herein, the micro-lenses 5002 have functions of condensing the lights, as is equal to the surfaces thereof on the photo-multiplier tubes 5001. Also, as is shown in FIG. 10(*b*), optical fibers 5004 may be attached via jigs 5003 provided in downstream of the micro-lenses 5002, and further the photo-multiplier tubes 5001 are attached to output terminals of the optical fibers 5004, in the structure thereof. In this instance, since the diameter of the optical fiber is smaller than that of the photo-multiplier tube 5001, the sensor pitch can be made smaller than that shown in FIG. 10(*a*); therefore, it is possible to build up a sensor having high resolution.

Next, explanation will be made about the side-directed detection optic system 600 within the detection optic system 200, by referring to FIGS. 1 and 11. Thus, in the inspection of foreign matters, due to high integration of the semiconductors, there is caused a necessity of making an inspection also upon a multi-layer wafer, which is increased in trend of the recent years. As is shown in FIG. 6, the multi-layer wafer is produced through repetition of a process of forming a transparent film (for example, an oxidation film) 800 and forming the circuit patterns on it, upon the surface of the wafer. Then, with an inspection on foreign matters on the wafer, a need goes up, in particular, for inspecting the defects 802, such as, very fine foreign matters and/or scratches on the surface of the transparent film 800.

Basically, by making the illumination angle α small with using the illumination light beams 220 and 230, it is possible to suppress the ill influences of the lights reflected and/or diffracted by the circuit patterns from the background 801; however, since much of the scattering lights, which are generated from the defects due to making the illumination angle α small, come to exit at a low angle in the form of a forward scattering lights, therefore an incident light lowers down to be less, upon the object lens 21 of the detection optic system 200, then it is impossible to detect the defects 802 on the transparent film 800 with stability. Also, if receiving the forward scattering lights at the low angle, but it means the detection of the regular reflection light, and therefore it is impossible to detect the defects 802.

Figure 11:
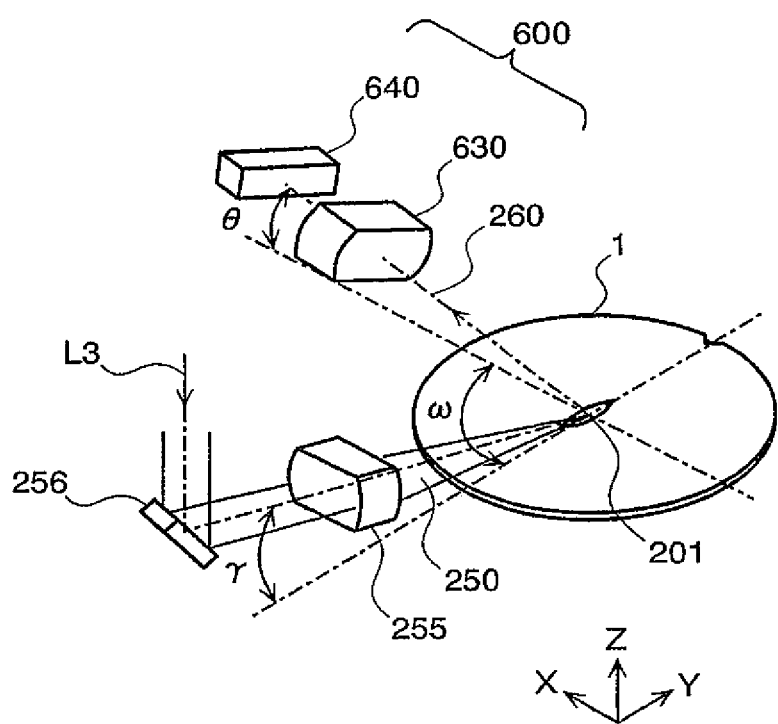
FIG. 11 is a brief structural view, for showing an embodiment of a side-directed illumination optic system and a side-directed detection optic system, according to the present invention.

Then, according to the present invention, as was mentioned above, the laser beam L3, which is enlarged on the beam diameter thereof, is irradiated upon the surface of the wafer 1 through the cylindrical lens 255, at the low illumination angle γ (approximately, from 5 degree up to 10 degree, for example), in the form of the illumination light beam 250, as shown in FIG. 11, and thereby forming the slit-like beam 201 having the longitudinal direction directed into the Y direction. However, as is shown in FIGS. 1 and 2(*b*), it is preferable to provide the cylindrical lens 225 in front of the mirror 256 on the optical path of the illumination light. And, the side-directed detection optic system 600 is disposed, with respect to the illumination light beam 250 generated from the fine foreign matters and/or the scratches or the like 802, lying on the transparent film 800 formed on the surface of the wafer 1, in such manner that it can detects mainly the side-directed scattered lights thereof at a low angle. For that purpose, that side-directed detection optic system. 600 comprises an image-forming optic system 630 and a photo-detector 640, each having an optical axis inclined by the low detection-angle θ (from 5 degree to 10 degree, approximately) from the direction intersecting the Y direction by an angle ω (for example, from 80 degree to 100 degree, approximately). Then, setup of the intersection angle ω in the vicinity of 90 degree brings the light-receiving surface of the photo-detector 640 to have a relationship of forming an image through the image-forming optic system 630, with respect to the slit-like beam 201, and it further allows setup of a magnifying power of image-forming within the image-forming optic system 630, so that the light-receiving surface of the photo-detector 640 can front on the entire illumination area or region of the slit-like beam 201. By bringing the side-directed detection optic system 600 into the relationship of forming such the image, at the low angle with respect to the slit-like beam 201, in this manner, it is possible to prevent ill influences of lights straying from other than the slit-like beam area; therefore, enabling parallel processing thereof, in the similar manner to the magnification-variable detection optic system 20, and obtaining high-speed of the inspection. Further, the photo-detector 640 can be built up with the TDI sensor or the photo-multiplier tubes, etc., in the similar manner to the photo-detector 26.

Also, during the inspecting operation, the surface of the wafer 1 stays at a constant position in the Z direction, while the photo-detector 640 is controlled by an automatic focus controller system not shown in figures, so that the light-receiving surface thereof can capture the entire illumination area of the slit-like beam 201. Also, with provision of the space filter within the optical path of the side-directed detection optic system 600, it is possible to shield the lights reflected and/or diffracted from the side of the circuit patters lying on the background and so on.

Further, with provision of devices on the image-forming optic system 630, it is possible to widen the area of the intersection angle ω mentioned above. Also, for the illumination light beam, if the inclination angle α thereof comes down to a low angle, it is possible to apply the illumination light beam 220 therein. In this instance, what can be detected by means of the side-directed detection optic system 600 is the detection of the scattering lights in the side-front (in the direction of 135 degree, seeing flatly). Also, when applying the illumination light beam 230 therein, it is sufficient to provide the side-directed detection optic system 600 between the mirrors 245 and 225, each of which has no interference between the illumination systems.

As was explained above, with provision of the side-directed detection optic system 600 for detecting mainly the side-directed scattered lights through forming it into the slit-like beam 201 at the low angle, it is possible to detect the defects, such as, the fine foreign matters and/or scratches on the transparent film 800, at high accuracy, but suppressing the ill influences due to the light reflected from the background.

Figure 12A:
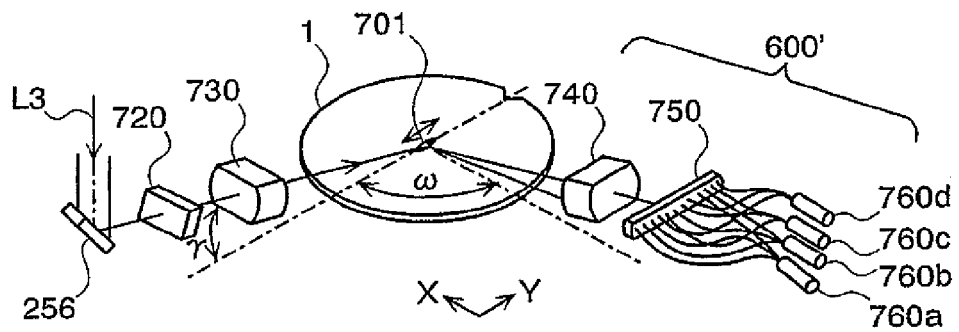
FIGS. 12(a) to 12(c) are views for explaining an embodiment of the photo-detector, being constructed with plural numbers of photo-multiplier tubes, for scanning an illumination spot, within the optic system shown in FIG. 11.
Figure 12B:
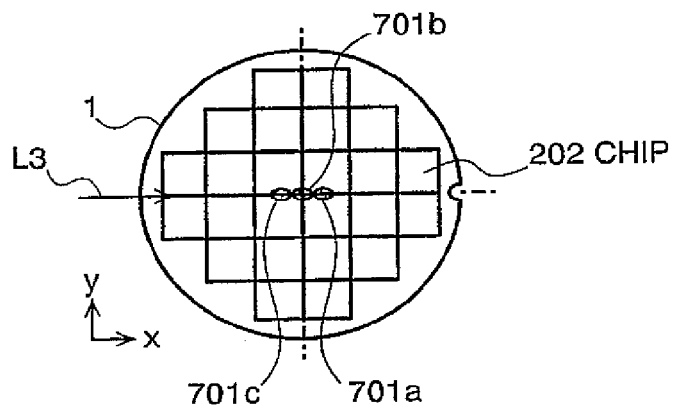
Figure 12C:
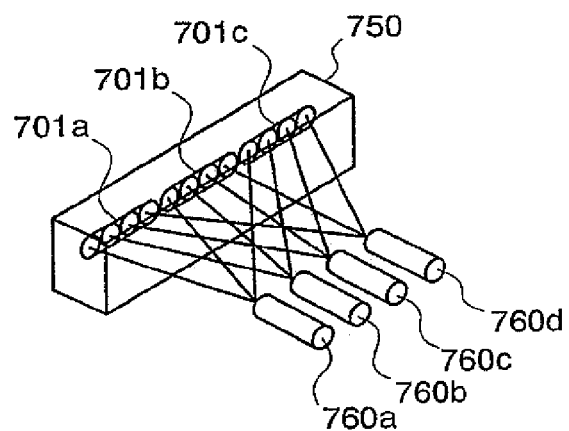

Also, as is shown in FIG. 12(*a*), scanning the laser light L3, for example, at high speed in the Y direction by means of a light deflecting means (i.e., a light deflector) 720, so as to obtain high-speed scanning of a spot 701, which is condensed and irradiated upon the surface of the wafer at the low angle γ through the condenser lens 730; thereby forming an image of the side-directed scattered lights generated from the defects 802, such as, the foreign matters and/or scratches, etc., upon the light-receiving surface of a distributor means 750, such as, the optical fibers, through the image-forming lens 740 at the low angle θ; thereby, it is possible to detect that optical image formed upon photo-electric conversion elements 760*a*-760*d*, such as, the photo-multiplier tubes, etc., for example, being guided by means of the distributor means 750 mentioned above. In the case of this embodiment, those elements attached with the reference numerals 740-760 build up a side-directed detection optic system 600'. In this case, as is shown in FIG. 12(*b*), forming spot scanning groups 701*a*-701*c* in plural numbers thereof on the wafer 1 enables to obtain high-speed in the scanning with use of the photo-multiplier tubes, or the like. Also, with detection of the scattered lights generated from each of the scanning spots 701*a*-701*c* due to the defects, as is shown in FIG. 12(*c*); optical information guided by the distributor means 750 can be signal-processed in parallel, through picking up on the photo-multiplier tubes 760*a*-760*d* at a constant interval, and therefore it is possible to make the inspection thereof at high speed. As a result of this, it is possible to reduce the number of the photo-multiplier tubes, thereby detecting the defects 802, without offset or deflection thereof. Thus, since the detection position of each of the photo-multiplier tubes is determined in the Y direction on the wafer, by applying the deflection signal of the light deflector 720 therein, it is sufficient to detect the signal of the defects detected from the each photo-multiplier tube in synchronism with the high-speed scanning of the spot 701.

Also, the laser light L3 is divided into plural numbers of laser lights 132*a*-132*d*, by means of a branching means 131 (131*a*-131*d*), and each of the laser lights 132*a*-132*d* is modulated in the intensity thereof, for example, with the frequencies being different from each other within optical modulators 133*a*-133*d*, upon basis of the signals from oscillators 134*a*-134*d*. And then, each of those laser lights 135*a*-135*d*, which are modulated in intensity thereof, is reflected upon mirrors 136*a*-136*d* and 137*a*-137*d*, and further it is deflected into the Y direction within an optical deflector 138, to be condensed through a condenser lens 139, thereby being irradiated upon the wafer 1 at the inclination angle γ in the form of multi-spots 140*a*-140*d*. Herein, each of the optical deflectors gives such an offset onto the deflection angle, that those spots will not overlap each other, completely, in the Y direction. With this can be obtained the multi-spots 140*a*-140*d*, which are modulated in the intensity thereof with frequencies different from one another and are scanned in the Y direction, entering at the inclination angle γ. On the contrary to this, the side-directed detection optic system comprises an image-forming lens 141, a light-receiving portion 142, optical fibers 143 connected with that light-receiving portion 142, and a photo-multiplier tubes 144. However, it is possible to build up the photo-detector with those, including the light-receiving portion 142, the optical fibers 143 and the photo-multiplier tubes 144. Reference numerals 145*a*-145*d* depict synchronization detector circuits, each detecting the frequency included in the signal components outputted from the photo-multiplier tubes 144 with an aid of the signals of respective frequencies, which are obtained from the respective oscillators 134*a*-134*d* and are applied to the respective optical modulators 133*a*-133*d*; thereby enabling to detect on which one of scanning of the spots 140*a*-140*d* the defects occurs. Thus, the photo-multiplier tubes 144 receive the side-directed scattering lights from the defects 802 through scanning of the multi-spots; however, with an aid of the signal indicative of the defects, which is detected from the respective synchronization detector circuits 145*a*-145*d* and outputted therefrom, it is possible to discriminate on which scanning of the spots 140*a*-140*d* generates that signal. As a result of this, the signal processing system 40 is able to calculate out a coordinate in the Y direction, of the position where the defects are generated, upon basis of the deflection signals (corresponding to the scanning signals on the wafer) from a controller circuit 146 for controlling the optical deflector 138.

As was explained above, irradiating the lights, each of which is modulated in intensity with frequencies differing from each other in each of the optical modulators 133*a*-133*d*, respectively, for example, and are scanned, in the form of the multi-spots 140*a*-140*d*, and extracting the signal indicative of the defects through detection of the signals detected by the photo-detectors through the respective synchronization detector circuits 145*a*-145*d*, it is possible to detect the defects while keeping the detection sensitivity to be uniform, in comparison with the case of irradiating lights in the form of the multi-spots while changing the wavelengths thereof, and thereby obtaining high-speed.

Also, in a case where no transparent film 800 is formed on the surface of the inspection target 2, it is not always necessary to set the inclination angle γ and the detection angle θ to be low in the angle, but they may be set at arbitrary value, within a range from 5 to 90 degrees.

Furthermore, in the place of scanning the plural numbers of laser spots, it is also possible to obtain high-speed of inspection, by disposing the plural numbers of detection heads, each of which is unified with the scanning laser illumination system and the detection optic system therein, into the direction of aligning the chips 202, in more preferably, fitting with the pitch of chips.

Figure 13:
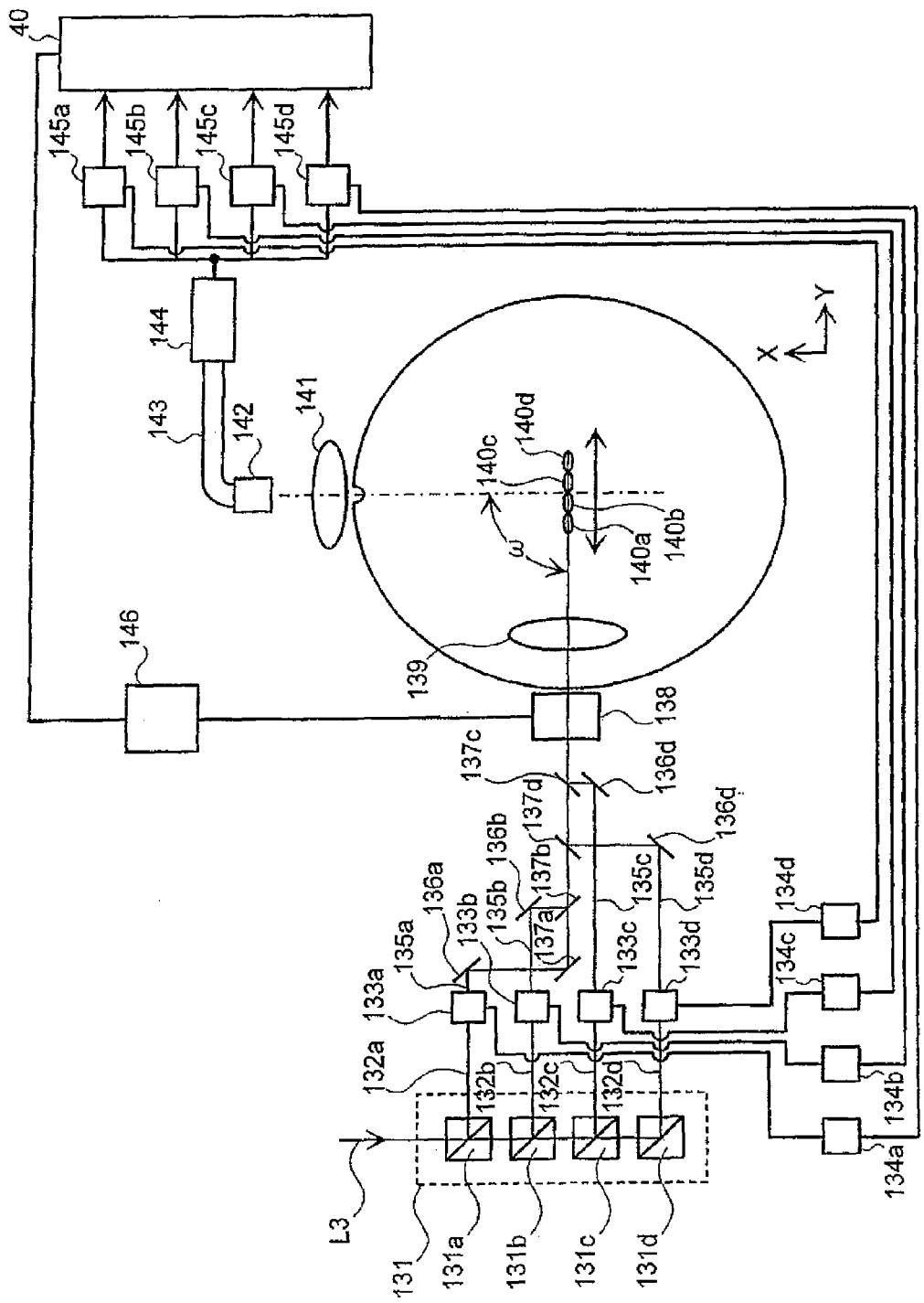
FIG. 13 is a brief structural view for showing other embodiment of the illumination system and the detection optic system, according to the present invention.

The technologies shown in FIGS. 12(*a*)-12(*c*) and FIG. 13 mentioned above are also applicable, for example, into the upper-directed detection of using the detection optic system 200 therein.

[Conveyer System 30]

Next, explanation will be made on the conveyer system 30. The stages 31 and 32 are for moving the sample-mounting base 34 on the XY plane, thereby having a function of enabling to move the entire surface of the inspection target substrate 1 within the illumination area of the illumination optic system 10. Also, the stage 33 is a Z stage, thereby having a function of enabling to move the sample-mounting base 34 into the direction of an optical axis (i.e., the Z direction) of the magnification-variable detection optic system 20. Further, the sample-mounting base 34 has a function of holding the wafer 1 thereon, as well as, of rotating the inspection target substrate 1 on the plane. And further, the stage controller 35 has a function of controlling the stages 31, 32 and 33, and also the sample-mounting base 34.

[Signal Processing System 40]

Figure 14:
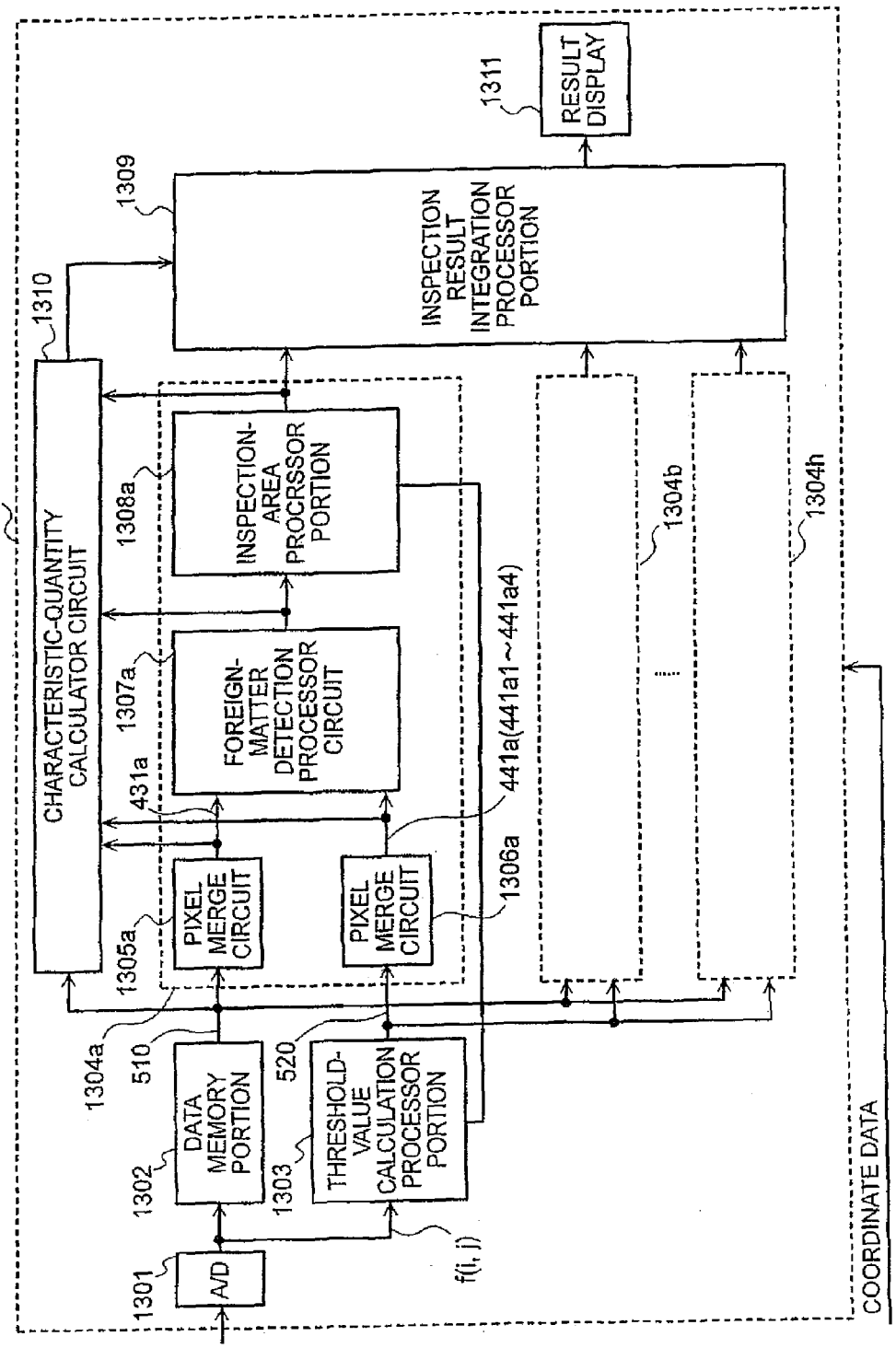
FIG. 14 is a view for showing the detailed structures of a signal processing system, according to the present invention.

Next, explanation will be given about the details of the signal processing system 40 for processing outputs from the photo-detectors 26 and 640, etc., by referring to FIG. 14. The signal processing system 40 comprises; an A/D converter 1301 for converting the signal, which is inputted from each of the photo-detectors 26 and 640, being exchanged therebetween; a data memory portion 1302 for memorizing detected image signal f(i,j) on which A/D conversion is made; a threshold value calculation processor portion 1303 for processing calculation of a threshold value upon basis of the detected image signal mentioned above; foreign-matter detection processor portions 1304a-1304n, each for conducting a foreign-matter detection process for each of pixel merges, upon basis of the detected image signal 510 obtained from the data memory portion 1302 mentioned above and the threshold value image signals (Th(H), Th(Hm), Th(Lm), Th(L)) obtained from the threshold value calculation processor portion 1303; a characteristic-quantity calculator circuit 1310 for calculating out characteristic quantities, such as, an amount of scattering lights obtained from defect detection through the low-angle illumination/the upper-directed detection (i.e., the low-angle illumination by means of the illumination light beams 220 and 230/the upper-directed detection by means of the photo-detector 200), an amount of the scattered lights obtained from defect detection through the high-angle illumination (including a middle-angle illumination)/the upper-directed detection (i.e., the high-angle illumination by means of the illumination light beams 220, 230 and 240/the upper-directed detection by means of the detection optic system 200), an amount of the scattered lights obtained from defect detection through the low-angle illumination/the oblique detection (i.e., the low-angle illumination by means of illumination light beam 250/the oblique detection by means of the side-directed detection optic system 600), and the detected number pixels indicative of an extent of the defects, etc., for example; an integrated processor circuit 1309 for classifying the defects, such as, small/large foreign matters or pattern defects or micro-scratches, etc., on the semiconductor wafer, into each kinds of those defects, upon basis of the characteristic quantity of each of the merges, which can be obtained from the said characteristic-quantity calculator circuit 1310; and a result display portion 1311. The foreign-matter detection processor 1304a-1304n are constructed with, each comprising pixel merge circuit portions 1305a-1305n, 1306a-1306n, foreign-matter detection processor circuits 1307a-1307n, and inspection area processor portions 1308a-1308n, corresponding to each of merge operators of, for example, 1×1, 3×3, 5×5, . . . n×n.

In particular, the present invention is characterized by, the foreign-matter detection processor portions 1304a-1304n, the characteristic-quantity calculator circuit 1310, and the integrated processor circuit 1309.

Next, explanation will be made about the operations thereof. First, the signal obtained from each of the photo-detectors 26 and 640, while exchanging therebetween, is digitalized within the A/D converter 1301. This detected image signal f(i,j) 510 is stored within the data memory portion 1302, at the same time, transmitted to the threshold-value calculation processor portion 1303. Within the threshold-value calculation processor portion 1303, calculation is made upon the threshold image Th(i,j), and within the foreign-matter detection processor circuits 1307, detection is made upon the foreign matters upon basis of the signal processed within the pixel merge circuits 1305 and 1306, for each of various kinds of merges. Upon the foreign-matter signal detected and/or the threshold image is treated a process depending upon the detection point or position, within the inspection area processor portion 1308. At the same time, upon basis of the signals obtained from the pixel merge circuits 1305a-1305n and 1306a-1306n, the foreign-matter detection processor circuits 1307a-1307n, and the inspection area processor portions 1308a-1308n of the foreign-matter detection processor portions 1304a-1304n, which are provided for each of the various merge operators, calculation is made on the characteristic quantity (for example, the amount of scattered lights obtained through the high-angle illumination/the upper-directed detection, an amount of the scattered lights obtained through the low-angle illumination/the upper-directed detection, an amount of the scattered lights obtained through the low-angle illumination/the oblique detection, and the number of detected pixels, etc.), and the foreign-matter signal and the characteristic quantity mentioned above are integrated within the integration processor portion 1309, and thereby displaying the inspection result on the result display portion 1311.

Hereinafter, the details of the above will be mentioned. Firstly, the A/D converter 1301 is a circuit, having a function of converting analogue signals, which are obtained from the photo-detectors 26, 640 and so on, into digital signals, but preferably has a conversion bit number from 8 bits to 12 bits, for example. This is, because of the facts that it is difficult to detect a minute light, since the smaller the bit number, the lower the resolution of the signal processing, but on the other hand, there is caused a demerit of increasing a price of the apparatus, since the A/D converter is expensive as the bit number comes up to be large. Next, the data memory portion 1302 is a circuit for memorizing the digital signals therein, on which the A/D conversion is made.

However, the threshold-value calculation processor portion 1303 is described in Japanese Patent Laying-Open No. 2000-105203 (2000). Thus, within the threshold-value calculation processor portion 1303, threshold-value image of the detection threshold values (i.e., Th(H) and Th(L)) and verification threshold values (i.e., Th(Hm) and Th(Lm)) is calculated out from the following equation (2). Where, a deviation of input data can be calculated out by $(\sigma(\Delta S) = \sqrt{\Sigma \Delta S^2/n - \Sigma \Delta S/n})$, and an averaged value of the input data by $(\mu(\Delta S) = \Sigma \Delta S/n)$. Further, it is assumed that a coefficient (i.e., the magnification) is "k" for setting up the threshold value corresponding to a number "n" of the input data, and that a coefficient is "m" (assuming that "m" is smaller than 1) for verification.

$$Th(H) = \mu + k \times \sigma,$$

or $$Th(H) = \mu - k \times \sigma,$$

or $$Th(Hm) = m + (\mu + k \times \sigma),$$

or $$Th(Lm) = m \times (\mu - k \times \sigma) \quad (2)$$

Or, the threshold-value image data may be changed for each of the areas, which are set up from the inspection area processor portions 1308a-1308n. In brief, for lowering the detection sensitivity within a certain area, it is sufficient to increase the threshold value in that area.

Figure 15:
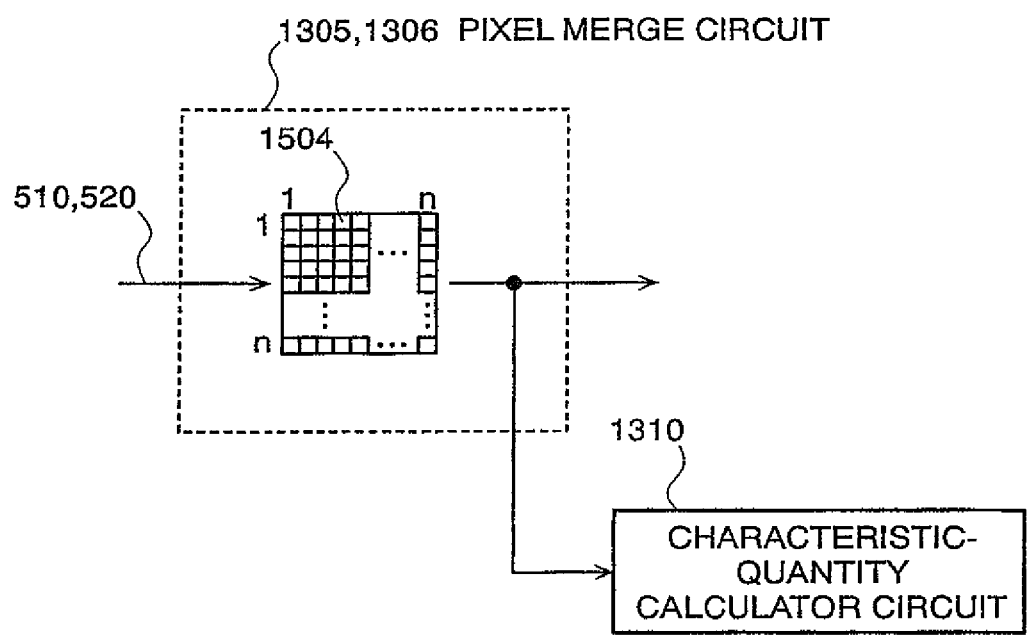
FIG. 15 is the structural view for showing a pixel merge circuit shown in FIG. 14.
Figure 16:
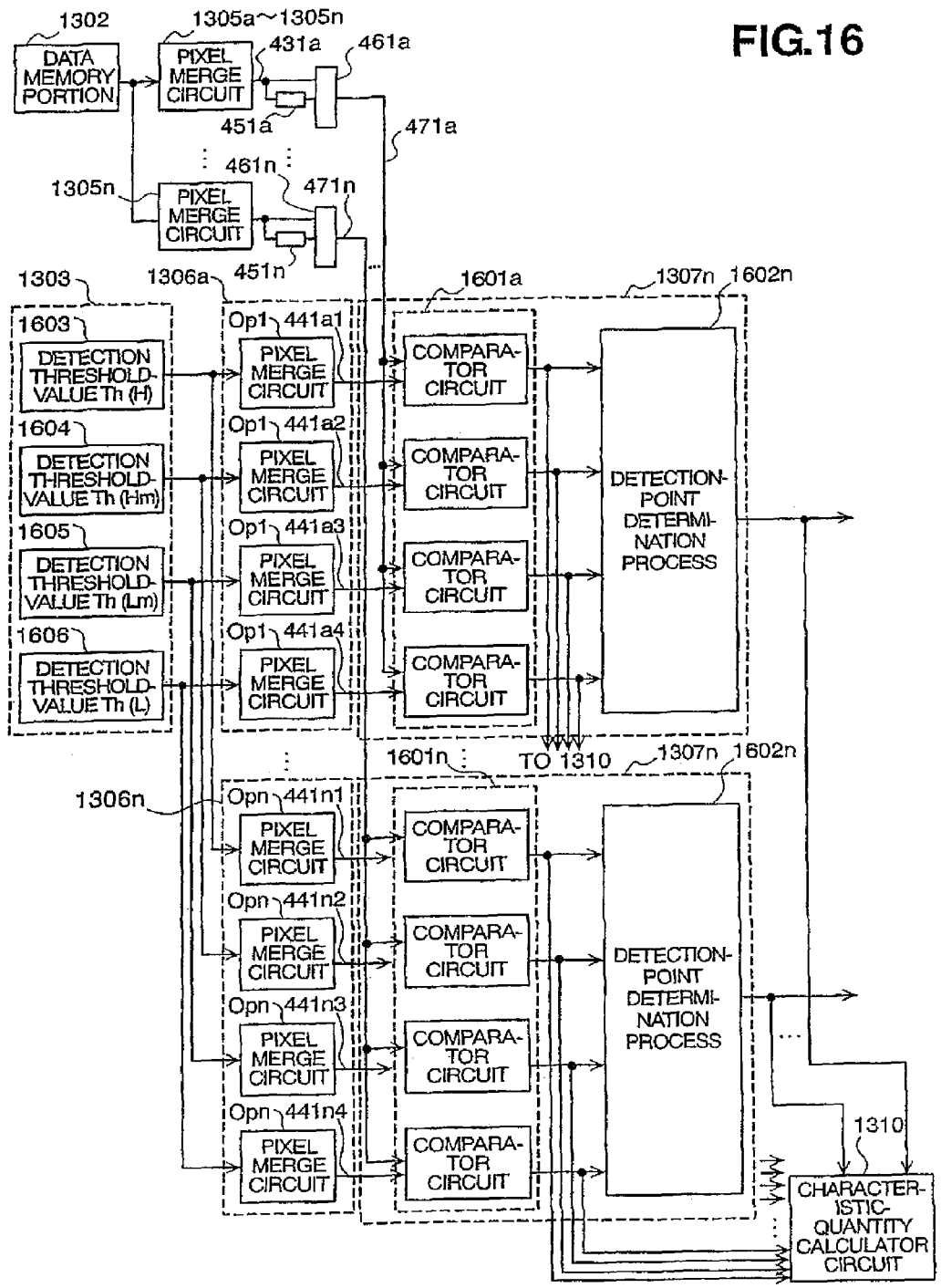
FIG. 16 is the structural view for showing a foreign-matter detection processor portion shown in FIG. 14.

Next, explanation will be give about the pixel merge circuit portions 1305 and 1306 for signals, by referring to FIGS. 15 and 16. The merge circuit portions 1305a-1305n and 1306a-1306n are constructed with merge operators 1504, each being different from each other. Each of the merge operators 1504 has a function of combining the detected image signal f(i,j), which can be obtained from the data memory portion 1302, and the threshold-value image signal 520, which can be obtained from the threshold-value calculation processor portion 1303, including the verification threshold-value images Th(H), Th(L), Th(Hm) and Th(Lm) within a region of n×n pixels for each, and it is a circuit for outputting an averaged value of n×n pixels, for example. Herein, the pixel merge circuit portion 1305a or 1306a is made up with the merge operator for merging 1×1 pixel, the pixel merge circuit portion 1305b or 1306b with the merge operator for merging 3×3 pixels, the pixel merge circuit portion 1305c or 1306c with the merge operator for merging 5×5 pixels, . . . and the pixel merge circuit portion 1305n or 1306n with the merge operator for merging n×n pixels, for example. Thus, the merge operator for merging 1×1 pixel provides the input signal 510 or 520 as it is, to be an output therefrom.

With the threshold image signals, since each one is made up with four (4) image signals (i.e., Th(H), Th(L), Th(Hm) and Th(Lm)), there is necessity of providing four (4) pieces of the merge operators Op in each of the pixel merge circuit portions 1305a-1306n. Accordingly, from each of those pixel-merge circuit portions 1305a-1306n are outputted the detection image signals, being treated with merge processing in the various kinds of merge operators 1504, in the form of merge-process detection image signals 431a-431n. On the other hand, from each of those pixel-merge circuit portions 1306a-1306n are outputted four (4) threshold image signals (Th(H), Th(Hm), Th(Lm) and Th(L)), being treated with the merge process thereon within the various kinds of merge operators Op1-Opn, in the form of merge-processed threshold-value image signals 441a(441a1-441a4)-441n(441n1-441n4). However, the merge operator within each of the pixel-merge circuit portions 1306a-1306n is same to one another.

Herein, explanation will be made about an effect of merging the pixels. With the foreign-matter inspecting apparatus according to the present invention, it is needed to detect, not only the fine or microscopic foreign matters, always, but also thin-film like foreign matters extending or spreading over a region of several μm, without looking over thereof. However, the image signal detected from the thin-film like foreign matters not always sufficiently large enough; i.e., the S/N ratio is low for a unit of one (1) pixel of the detection image signal, and therefore, resulting into the look over thereof, sometimes. Therefore, if bringing the level of the detection image signal averaged for one (1) pixel up to S and dispersion of averaging be σ/n, then the level of the detection signal comes to be $n^2 \times S$ through conducting the convolution operation upon the pixels, which are cut out by a unit of n×n pixels corresponding to the size of the thin-film like foreign matters, while the dispersion (N) is σ×n. Accordingly, the S/N ratio is n×S/σ. Therefore, through the convolution operation while cutting out the pixels by a unit of n×n corresponding to the thin-film like foreign matters, it is possible to increase the S/N ratio up to that by n times.

With the fine or microscopic foreign matters of about one (1) pixel unit in the size, since the detected image signal level is S and the dispersion is σ, which can be detected by the one (1) pixel unit, therefore the S/N ratio is S/σ. If conducting the convolution operation upon the n×n pixels, which are cut out with respect to the fine foreign matters of about one (1) pixel unit, then the detected image signal level is $S/n^2$ and the dispersion is n×σ; therefore, the S/N ratio is $S/n^3/\sigma$. Accordingly, with such the fine or microscopic foreign matters of about one (1) pixel unit in the size, an improvement can be obtained if applying the signal of the pixel unit as it is.

Although the explanation was made about the example, in which the merge area or region is a regular square (i.e., n×n pixels), in the present embodiment; however, the merge area may be an oblong (i.e., n×m pixels). In this instance, detection of the foreign matters having directional property (i.e., the orientation) can be made in the form of the oblong, as well as, the detecting pixels on the photo-detectors 26 and 640; however, it is effective to process the signal processing in the square form.

Also, though the explanation was made about the embodiment of outputting the average value of n×n pixels, in particular, as the function of the merge operator; however, a maximum value, a minimum value or a central value of the n×n pixels may be outputted therefrom. In the case of applying the central value, there can be obtained a stable signal. Further, as an output value may be a value, which can be obtained through multiplying or dividing the average value of the n×n pixels by a specific value.

Next, FIG. 16 is a view for showing an embodiment of the foreign-matters detection processor circuit 1307. In this FIG. 16, the details are shown of the pixel merge circuit portion 1305a and 1306a, each for merging the n×n pixels, and also of the pixel merge circuit portion 1305n and 1306n, each for merging the n×n pixels.

And, the foreign-matter detection processor circuits 1307a-1307n are constructed with comparators 1601a-1601n for comparing the levels of merge-process difference signals 471a-471n and merge-process threshold signals 441a-441n, respectively, and detect-position determination processor portions 1602a-1602n for identifying detecting points or positions of the foreign matters. In the comparator circuits 1601a-1601n are provided delay memories 451a-451n for delaying the detected image signals, which are obtained from the pixel merge circuits 1305a-1305n and are treated with the pixel merge thereupon, for repetition formed, such as, on a chip, for example, and difference processor circuits 461a-461n for forming difference signals between the detected image signals 431a-431n and reference image signals, which are delayed through the delay memories mentioned above and are treated with the pixel merge thereupon. Accordingly, the comparator circuits 1601a-1601n are those for making comparison with the merge-process threshold value image Th(H) (i,j), Th(Hm)(i,j), Th(Lm)(i,j) and Th(L)(i,j), which are obtained from four (4) pieces of the pixel merge circuits Op of each of the pixel merge circuit portions 1306a-1306n, and have a function of determining the foreign matters, if the merge-process difference detection signals 471a-471n are larger than the merge-process threshold value image Th(i,j), for example. In the present embodiment, there are prepared four (4) kinds of the threshold values, thereby conducting the determination process upon merge-process threshold value images 1603, 1604, 1605 and 1606, for each of the merge operators, within the comparator circuits 1601a-1601n.

Next, explanation will be made about the detect-position determination processor portions 1602a-1602n. The process of detection-position determination is that for identifying the chip, on which the foreign matters or the defects lies thereon, corresponding to the various kinds of merge operators, thereby calculating out the positional coordinates (i,j). The way of thinking of the present process is to identify the chip, on which the foreign matters or the defects are detected, by using the results detected through the detection threshold values (i.e., Th(H) and Th(L)) and the verification threshold values (i.e., Th(Hm) and Th(Lm)), which are the threshold values smaller than the said detection threshold values in the value thereof.

Next, explanation will be made about the inspection area processor portions 1308a-1308n. The inspection area processor portions 1308a-1308n are used when deleting data of an area (including an area within the chip) where no inspection must be made, or when changing the detection sensitivity for each of the areas (including an area within the chip), or on the contrary when selecting an area to be inspected, with respect to the detected signals of foreign matters and/or defects, which can be obtained from the foreign-matter detection processor circuits 1307a-1307n by identifying the chip. Within those inspection area processor portions 1308a-1308n, in particular, in a case where the detection sensitivity can be lowered down, within the area on the inspection target substrate 1, it is possible to set the threshold value to be high, for that area, which can be obtained from a threshold value calculator portion (not shown in figures) of the threshold-value calculation processor portion 1303, or apply a method of remaining only the data of foreign matters within the area where the inspection should be made, among the data of foreign matters outputted from the foreign-matter detection processor circuits 1307a-1307n, upon basis of the coordinates of the foreign matters.

Herein, the area where the detection sensitivity can be lowered down means an area having a low density of the circuit patterns on the inspection target substrate 1, for example. An advantage of lowering down the detection sensitivity lies in that the number of pieces of detections can be reduced down, effectively. Thus, with the inspecting apparatus having high sensitivity, sometimes, it detects the foreign matters of several-tens thousand (10,000) pieces thereof. In such the instance, what being truly important or serious are the foreign matters lying within the area where the circuit patters are formed, and it is the nearest way for improving yield or productivity in device manufacturing to take countermeasure to deal with such serious foreign matters. However, in the case where the inspection is made all over the area or region on the inspection target substrate 1 with the same sensitivity, since the serious foreign matters are mixed up with non-serious foreign matters, it cannot be made, easily, to extract the serious foreign matters. Then, within the inspection area processor portions 1308a-1308n, upon basis of CAD information or threshold map information within the chip, it is possible to extract the serious foreign matters with high efficiency, by lowering the detection sensitivity in the areas, which give no ill effect or influence upon the yield rate or productivity. However, as the method of extracting foreign matters, there may be applied others than that of changing the detection sensitivity, but it is also possible to extract the serious foreign matters through classifying the foreign matters, which will be mentioned later, or to pick up the serious foreign matters upon basis of the sizes thereof.

Next, explanation will be made about the integration processor portion 1309 and the inspection result display portion 1311 thereof. The integration processor portion 1309 has a function of integrating the foreign-matter detection results, which are processed in parallel within the pixel merge circuits 1305 and 1306, or integrating the characteristic quantities, which are calculated out within the characteristic-quantity calculator circuit 1319, and the detection results of foreign matters, and/or transmitting the results to the result display portion 1311. Preferably, the integration process of those inspection results is conducted with an aid of a PC, etc., for making the process contents being easily changeable.

First of all, explanation will be made on the characteristic-quantity calculator circuit 1310. This characteristic quantity means a value, indicative of the feature or characteristics of the detected foreign matters and/or defects, and the characteristic-quantity calculator circuit 1310 is a processor circuit for calculating out the characteristic quantity mentioned above. As the characteristic quantity, there can be listed up, for example, an amount of lights reflected and/or diffracted upon the foreign matters and/or defects (i.e., an amount of scattered lights) (Dh and Dl), which are obtained through the high-angle illumination/the upper-directed detection, the low-angle illumination/the upper-directed detection, and the low-angle illumination/the oblique detection, the number of detecting pixels, the configuration of the foreign-matter detecting area and the direction of an inertia main axis thereof, the detecting position of foreign matters on the wafer, the kinds of circuit patterns on the background, and the threshold values when detecting the foreign matters, etc.

Next, explanation will be made about an embodiment of DFC within the integration processor portion 1309.

Figures 17, 18:
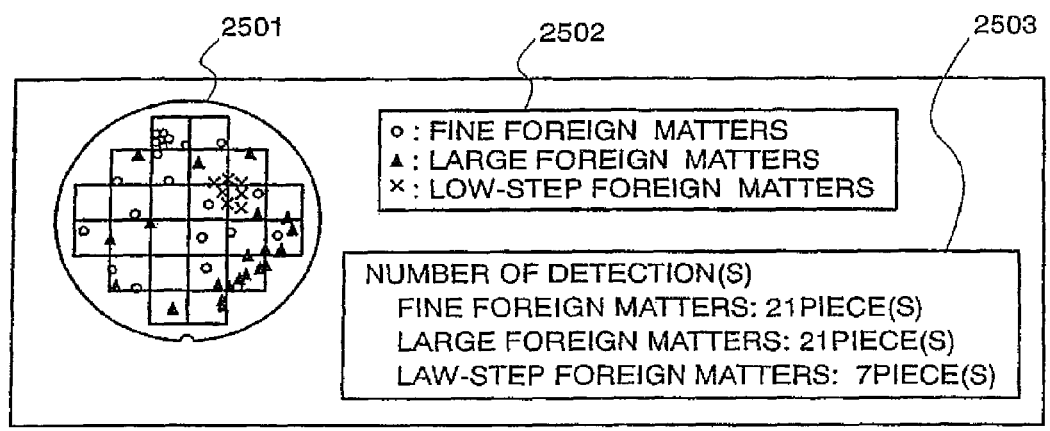
FIG. 17 is a view for explaining about a method, for classifying defects, including the foreign matters, etc., for example.
FIG. 18 is a view for showing an example of displaying a result of inspection, in particular, when classifying the defects, including the foreign matters, etc., for example.

Thus, since being inputted with the foreign-matter detection signals, upon which various kinds of pixel merges are treated, then the integration processor portion 1309 is able to classify the foreign matters into "large foreign matters", "fine foreign matters", "foreign matters having a low height", as shown in FIG. 17. This FIG. 17 is a table for showing the relationships between the classifying criteria and classified results. This FIG. 17 shows an example of applying the detection result between the result, which is detected through the 1×1 pixel and treated with the merge process thereupon, and the result, which is detected through the 5×5 pixels and treated with the merge process thereupon. Thus, from the foreign-matter detection processor circuits 1307a and 1307c can be obtained the inspection results upon the 1×1 pixel and the 5×5 pixels through the signal processor circuit. With using those, the classification is conducted according to FIG. 17. Thus, a certain foreign matter can be detected upon both the 1×1 pixel and the 5×5 pixels, and it is classified to be "large foreign matters". Also, if it can be detected upon the 1×1 pixel but not upon the 5×5 pixels, then it is classified to be "fine foreign matters", and further if it cannot be detected upon the 1×1 pixel but upon the 5×5 pixels, then it is classified to be "foreign matters having a low height".

FIG. 18 shows an embodiment of the display of inspection results, including therein the classifying results mentioned above. The display of the inspection results mentioned above is made up with position information 2501 of the foreign matters obtained from the detect-position determination processor portions 1602a and 1602c, category information 2502 of the classifying results obtained from the integration processor portion 1309, and numbers of foreign matters for each of the categories. With the present embodiment, the position of foreign matters is displayed through the position information of the said foreign matters, at the same time displaying the classification categories thereof with an aid of display marks, together. Also, the contents for each of the marks of classification categories are shown within the classification category information 2502. Further, the number of foreign matters 2503 for each category indicates the number of pieces of the foreign matters, which are classified into each of the categories. Changing the display for each of the categories in this manner, there can be obtain an advantage of seeing the distribution of each the foreign matters at a glance.

Next, explanation will be made about an embodiment of a method, for measuring the sizes of foreign matters, according to the present invention. The present method is one of utilizing the fact that there is a proportional relationship between the sizes of foreign matters and the light amount detected upon the photo-detector 26. Namely, in particular, if the foreign matters are small, there is the relationship that the light amount D detected is in proportional to $6^{th}$ power of the size G of the foreign matters, in accordance with the theory of scattering of Mie. Accordingly, the characteristic-quantity calculator circuit 1310 is able to measure the size of foreign matters from an equation (3), which will be shown below, upon basis of an amount D of the detected lights, the size G of foreign matters, and a proportional coefficient $\epsilon$, and thereby it provides it to the integration processor portion 1309.

$$G = \epsilon \times D^{(1/6)} \qquad (3)$$

Where, the proportional coefficient $\epsilon$ may be obtained from the light amount detected from the foreign matters, which size is already known, in advance, thereby to be inputted thereto.

Next, explanation will be made on an embodiment of the method for calculating out the detected light amount D, by referring to FIGS. 19(a) and 19(b). FIG. 19(a) shows an image of the fine foreign matter portion, which is produced upon basis of digital image signal of the fine foreign matters (i.e., the image signal obtained through A/D conversion upon the signal of the photo-detector 26), which can be obtained from the data memory portion 1302, in relation to the fine foreign matters detected within the foreign-matter detection processor circuit 1307. The fine foreign matter portion 2601 indicates the signal of the fine foreign matters. FIG. 19(b) shows A/D conversion values (i.e., gradation values of the pixels, for each) of the fine foreign matters 2601 shown in FIG. 19(a) and an image in vicinity thereof. This example shows an example when conducting the A/D conversion of 8 bits, wherein the foreign-matter signal portion 2602 indicates the detected signal from the fine foreign matters. Herein, "255" at a center of the foreign-matter signal portion 2602 indicates that an analog signal is in saturation, and portions of "0" other than the foreign-matter signal portion 2602 indicate that they are signals obtained from others than the fine foreign matters. As a method for calculating out an amount D of detected lights from the fine foreign matters, the sum is calculated out of the respective pixel values of the foreign-matter signal portion 2602 shown in FIG. 19(b). For example, in the example of FIG. 19(b), the detected light amount D of the fine foreign matters 2601 is "805", i.e., the sum of the values of the respective pixels.

Next, explanation will be made about another embodiment of method for calculating out the detected light amount D. The way of thinking in the present embodiment lies in that, the saturated portion of the foreign matter signal portion 2602 shown in FIG. 19(b) is compensated with an aid of approximation of the Gauss distribution; thereby, obtaining an improvement of accuracy of calculation of the detected light amount. About this compensation will be made explanation, by referring to FIG. 20. This FIG. 20 is a view for presenting the Gauss distribution in the three dimensional (3D) manner. This FIG. 20 shows the case where the signal is saturated at $y=y_0$, and a method that will be explained hereinafter, about calculating out the detected light amount of the entire Gauss distribution, in the portion below $y=y_0$ shown in FIG. 20; i.e., in the case where the detection light amount can be obtained in a portion of $V_3$. First of all, it is assumed that a volume of the entire Gauss distribution shown in FIG. 20 is $V_1$, that of portion above $y=y_0$ $V_2$, and that of portion below $y=y_0$ $V_3$, respectively. It is also assumed that the cross-section configuration can be obtained from the following equation (4) on the x-axis of the Gauss distribution shown in FIG. 20:

$$y = \exp(-x^2/2/\sigma^2) \qquad (4)$$

In this instance, $V_1$ can be expressed by the following equation (5) through conducting integration around the y-axis:

$$V_1 = 2 \times \pi \times \sigma^2 \qquad (5)$$

Further, $V_2$ can be expressed by the following equation (6):

$$V_2 = 2 \times \pi \sigma^2 (y_0 \times \log(y_0) + 1 - y_0) \qquad (6)$$

Where, "log" in the above equation is indicative of calculation of the natural logarithm.

Herein, rewriting a volume ratio $V_1/V_3$ to be CC, since CC can be calculated by the following equation (7), the following equation (8) can be calculated from the equations (5) and (6) mentioned above:

$$CC = V_1/(V_1 - V_2) \qquad (7)$$

$$CC = 1/(y_0 \times (1 - \log(y_0))) \qquad (8)$$

Herein, assuming that signal width of the saturated portion is SW, since it can be expressed by the following equation (9), then CC can be expressed by the following equation (10):

$$y_0 = \exp(-SW^2/2/\sigma^2) \qquad (9)$$

$$CC = \exp(SW^2/2/\sigma^2)/(1 + SW^2/2/\sigma^2) \qquad (10)$$

Accordingly, if the detected light amount is $V_3$, which is obtained as is shown in FIG. 19(b), the volume $V_1$ of the entire Gauss distribution can be calculated by the following equation (11), and therefore it is enough to put this $V_1$ into the detected light amount after compensation. However, it is necessary to calculate out the signal width SW:

$$V_1 = V_3 \times \exp(SW^2/2/\sigma^2)/(1 + SW^2/2/\sigma^2) \qquad (11)$$

As was mentioned above, the explanation was made about the method for calculating the detected light amount D, however in the case of a view field of the magnification-variable detection optic system 20 is wide, there might be a case where an error is caused due to distortion of the lens within the view field. In this case, compensation may be made corresponding to the lens distortion thereof.

In the present embodiment, although using the value of the sum of signals of the foreign-matter signal portion 2602 as the detected light amount, however it should not always the sum of signals, but it may be the maximum value of the foreign-matter signal portion 2602. As an advantage of the case of using the maximum value, it is possible to make the scale of electric circuitry small, and in the case of using the sum of signals, it is possible to reduce sampling errors on the signals, thereby obtaining a stable result.

Furthermore, with the display screen, it may be displayed on a display means 52, which is provided within the total controller portion 50.

Figure 21:
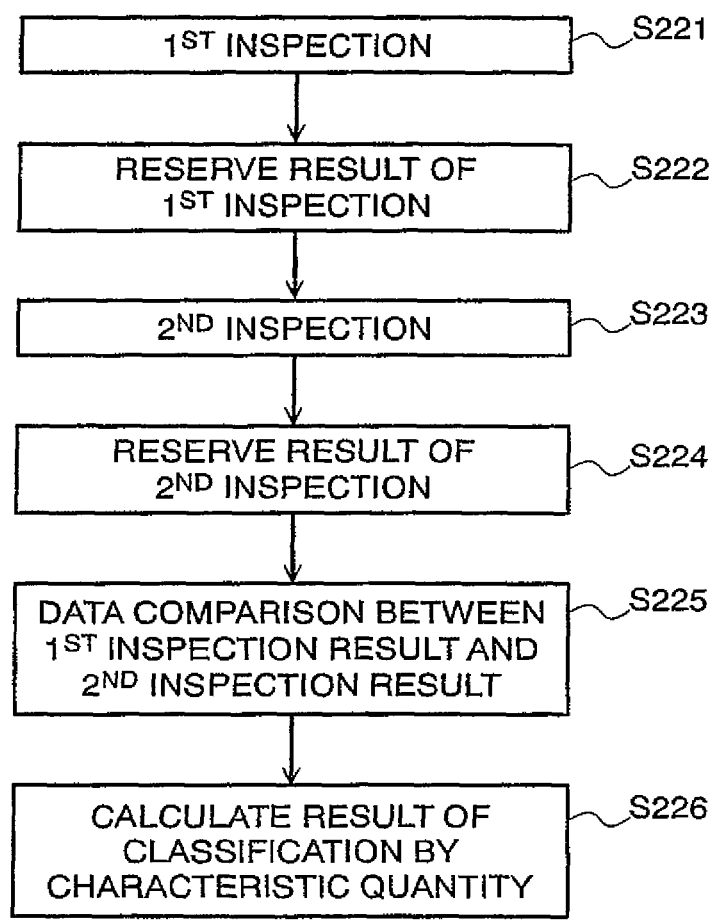
FIG. 21 a view for showing a sequence, according to other embodiment, in particular, relating to classification of the defects, including the foreign matters, etc., for example.

Next, explanation will be given about other embodiment of classification of foreign matters or defects, which is conducted within the integration processor portion 1309, by referring to FIG. 21 and FIGS. 22(a) and 22(b). FIG. 21 shows a sequence of classifying the foreign matters upon basis of the results, which are obtained through conduction of inspection by two (2) times made within the integration processor portion 1309.

Firstly, inspection is made upon the wafer 1 under a first inspection condition (S221). In the first inspection, the coordinate data of the foreign matters, which can be obtained from the foreign-matter detection processor circuit 1307, and the characteristic quantities of the respective foreign matters, which can be obtained from the characteristic-quantity calculator circuit 1310, are reserved within a memory device (not shown in the figure) (S222). Next, inspection is made upon the wafer 1, but under a second inspection condition different from the first inspection condition (S223), and in this second inspection, the coordinate data of the foreign matters obtained from the foreign-matter detection processor circuit 1307, and the characteristic quantities of the respective foreign matters obtained from the characteristic-quantity calculator circuit 1310, are also reserved within the memory device (not shown in the figure) (S224). In this instance, for example, if irradiating the illumination lights from an angle near to the wafer surface under the first inspection condition, for example, then as the second inspection condition, it is preferable to select a condition of irradiating the illumination lights from an angle near to a normal line on the wafer surface (i.e., a high-angle illumination condition). Also, when making an inspection upon the wafer 1 under the second inspection condition, the characteristic quantity at the coordinates where the foreign matters are detected under the first inspection condition is memorized, irrespective of detecting or not of foreign matters under the second inspection condition.

Next, comparison is made between the coordinate data obtained as the result of the first inspection and the coordinate data obtained as the result of the second inspection (S225), and then classification is made from the respective characteristic quantities thereof, while assuming that the foreign matters near to each other in the coordinates thereof be the same thing (S226). Herein, as one embodiment of the method for determining vicinity of the coordinate data, if assuming that the coordinate data obtained from the first inspection result are "$x_1$" and "$y_2$", that the coordinate data obtained from the second inspection result are "$x_2$" and "$y_2$", and that a comparison radiator is "r", then determination may be made that the data fitting to the following equation (12) to be the same thing:

$$(x_1-x_2)^2+(y_1-y_2)^2<r^2 \qquad (12)$$

Herein, "r" may be set to be zero (0) or a value by taking the error accompanying the apparatus into the consideration. As the measuring method, for example, calculation may be made upon the value of left-hand side of the equation (12) with the coordinate data of the foreign matters at several points, and then from the averaged value thereof and a standard deviation value, the value calculated out from the equation (13) may be set to "r", for example.

$$r^2=\text{average value}+3\times\text{standard deviation} \qquad (13)$$

Further, explanation will be made about the method for classifying the foreign matters from the foreign-matter information considered to be the same thing, by referring to FIGS. 22(a) and 22(b). In FIG. 22(a), onto the horizontal axis thereof is set the scattered light amount (Dl) obtained by the first inspection mentioned above (i.e., the low-angle illumination), while onto the vertical axis the characteristic quantity, i.e., the scattered light amount (Dh) obtained by the second inspection (i.e., the high-angle illumination). In FIG. 22(b), onto the horizontal axis thereof is set the scattered light amount (Dl') obtained from the side-directed detection optic system 600 under the low-angle illumination, while onto the vertical axis is set the scattered light amount (Dh') obtained therefrom under the high-angle illumination. In those FIGS. 22(a) and 22(b), a reference numeral 3501 depicts points, being plotted corresponding to each of the characteristic quantities of the foreign matters, which are considered to be the same thing. In the present embodiment, one (1) point indicates one (1) piece of foreign matter. Also, a reference numeral 3502 depicts a classification curve for classifying the foreign matters detected during the inspection. Those FIGS. 22(a) and 22(b) show a case of dividing into two (2) areas by the classification line, i.e., an area 3503 and an area 3504. As a method for classifying, if the above-mentioned foreign matters detected should be plotted within the area 3503 in FIG. 22(a), they are classified to be "large foreign matters or scratches", while they are classified to be "small foreign matters" if they should be plotted within the area 3504. Also, detected things 4510 are classified to be the defects within film, lying inside the transparent film 800, if the scattered light amount (Dl') within the side-directed detection optic system 600 is smaller, comparing to the scattered light amount (Dl) under the low-angle illumination and the scattered light amount (Dh) under the high-angle illumination, as is shown in FIG. 22(a). By the way, in the case of an upper-directed detection under the low-angle illumination, the brightness comes down due to spreading of the illumination light beam upon the wafer, thereby lowering the sensitivity; therefore, the detection sensitivity of the upper-directed detection is lower than that of the side-directed detection.

Herein, it is necessary to determine the classification line 3502, in advance. As a method for determining it in advance, plotting the detected things in several numbers thereof on a graph of FIGS. 22(a) and 22(b), which are already known to be the large foreign matters or the small foreign matters in advance, the classification line 3502 is set up, so that the detected things can be divided, correctly. Or, calculating out the characteristic quantity obtainable from the foreign matters, through simulation thereon, the classification line 3502 may be set up from the result thereof. Herein, as a method of affirming the kinds of foreign matters, for example, the classification may be made with using the detected things upon the wafer, which are already known about the defects coordinate and the kinds thereof through a review apparatus, such as, an observatory optic microscope 60 or a SEM, etc., which is mounted within the inspecting apparatus. With the review apparatus, including the observatory optic microscope 60 mounted within the inspecting apparatus, it is possible to make the classification within a short time, while in the case of using the SEM, it is possible to make the classification with high resolution. The detected things are the foreign matters, the scratches, or the foreign matters within transparent film, etc., in the kind thereof. Upon setup of the classification line 3501, the threshold value may be set at such a certain value of the scattered light amount obtainable under the low-angle illumination, that there occurs no error of detecting electric noises within the detector 26 to be the foreign matters. Also, firstly calculation is made upon a position of the center of gravity, for each of the groups of large foreign matters and small foreign matters, thereby obtaining the standard deviation at each of the plotted points therefrom. Next, an orthogonal bisector is drawn, as the classification line 3502, at a point on a straight line, satisfying L×(r1/r1+r2)), where distance is "L" of a line joining between the respective positions of the center of gravity, and radii of the standard deviation from the respective positions of the center of gravity are "r1" and "r2", respectively.

In the present embodiment, though the explanation was given about the example of conducting the inspection two (2) times; however, in a case where an improvement can be obtained upon the classifying performances when increasing up the kinds of the characteristic quantities (for example, the detecting pixel number: corresponding to an area Q of the defect), the characteristic quantities (i.e., detecting pixel number) may be obtained of the foreign matters, by conducting the inspection three (3) times thereupon.

Figure 23:
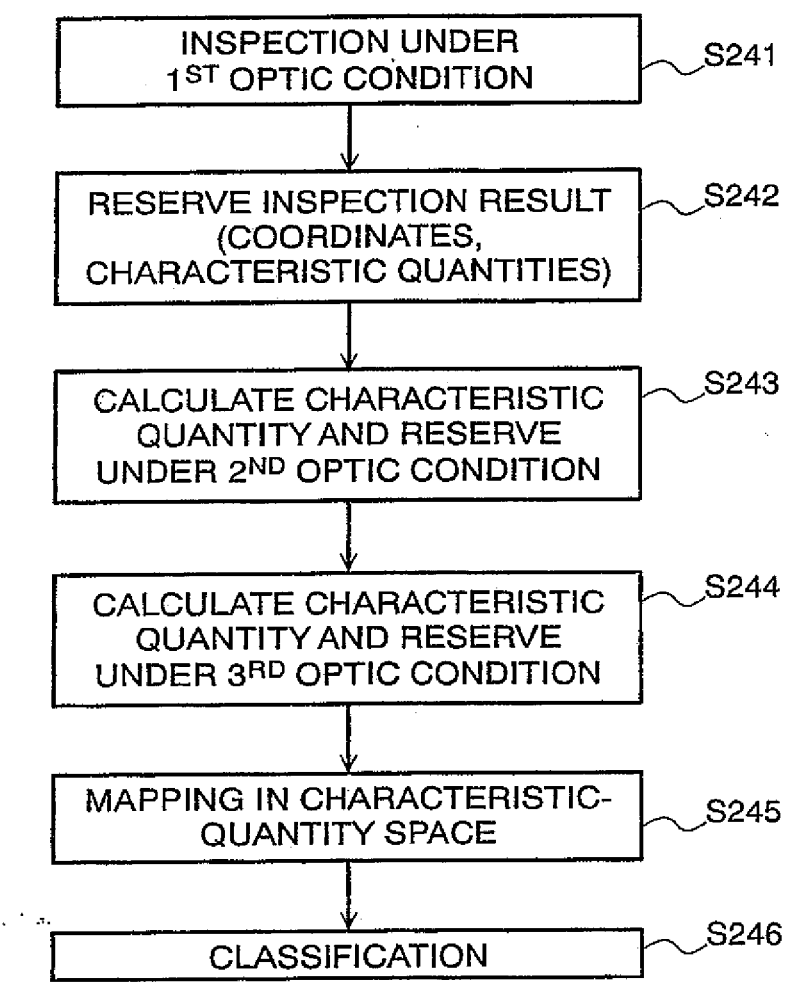
FIG. 23 is a view for showing a sequence, according to further other embodiment, in particular, relating to classification of defects, including the foreign matters, etc., for example.

Next, explanation will be given about further other embodiment of the classification of foreign matters or defects, which will be executed within the inspection result integration processor portion 1309, by referring to FIG. 23. This FIG. 23 shows a sequence of an embodiment for making the classification with using the characteristic quantities, being calculated upon three (3) kinds of optical conditions after conducting the inspection only one (1) time.

First, inspection is made upon the wafer under the first optical condition (S241), and reservation is made on both the coordinate data of foreign matters, obtained from the foreign-matter detection processor circuit 1307, and the characteristic quantities for each of the defects, obtained from the characteristic-quantity calculator circuit 1310 (S242). Next, the optical condition is changed in the foreign-matter inspecting apparatus according to the present invention. This includes, for example, the irradiation angle and/or the illumination direction of the illumination optic system, and/or the detecting direction (i.e., the upper-directed or the oblique) by means of the detection optic system. Also, the magnification (or, magnifying power) of the detection optic system may be changed, or the optical filters may be exchanged. It is assumed that the second optical condition is that, upon which such changes as mentioned above can be made.

After changing the optical condition into the second optical condition, the wafer 1 is moved on the conveyer system 30, to the position on the coordinate of the foreign matters, which are reserved, as was mentioned above, then upon basis of the detected image signal, which can be detected upon the photo-detector 26 and obtained through A/D conversion thereof under the second optical condition, the characteristic quantities of foreign matters are calculated out within the characteristic-quantity calculator circuit 1310 (S243). Further, calculation will be made in the similar manner, when calculating out the characteristic quantities under the third optical condition (S244). In this instance, it is preferable that the first optical condition, the second optical condition and the third optical condition differ from one another, respectively.

Figure 24:
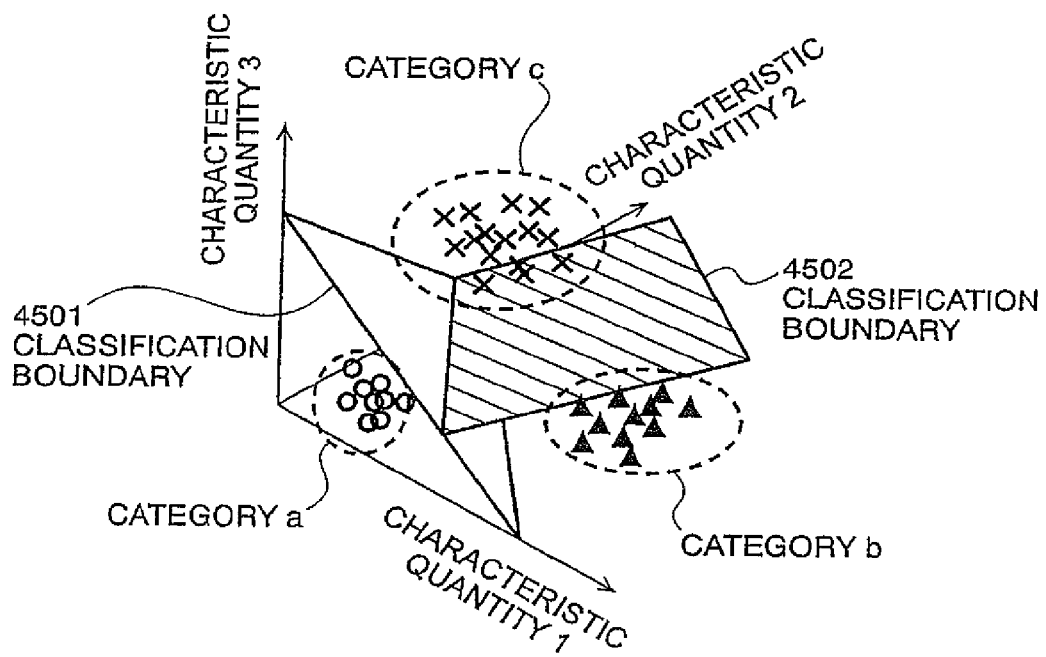
FIG. 24 is a view for explaining about the method for classifying the defects, including the foreign matters, etc., from plural kinds of characteristic quantities thereof.

The way of thinking of this classifying method will be explained by referring to FIG. 24. This FIG. 24 shows a characteristic quantity space, in which the three (3) kinds of characteristic quantities are setup to the three (3) axes thereof. As those three (3) axes, for example, a characteristic quantity 1 is the characteristic quantity (for example, the scattered light amount (Dh)) obtained from defects under the first optical condition (for example, the high-angle illumination), the second characteristic quantity 2 is the characteristic quantity (for example, the scattered light amount (Dl)) obtained from defects under the second optical condition (for example, the low-angle illumination), and a third characteristic quantity is the characteristic quantity (for example, the detecting pixel number: a flat area of the defects) obtained from defects under the third optical condition (for example, the high-angle illumination of being the first optical condition and the low-angle illumination of being the second optical condition). In such the characteristic space, (number of classification categories—1) pieces of classification boundaries are set up. Since this FIG. 24 shows an example of conducting the classification into three (3) kinds from three (3) kinds of characteristic quantities, therefore it is sufficient to setup the classification boundaries in the number of two (2) or more than that.

In particular, as those three (3) kinds of characteristic quantities, if setting up the scattered light amount (i.e., the detection light amount) (Dh) from defects under the high-angle illumination, the scattered light amount (i.e., the detected light amount) (Dl) from defects under the low-angle illumination, and the detecting pixel numbers of defects under the high-angle illumination and the low-angle illumination, it is possible to classify the defects, at least, into three (3) kinds of categories (the foreign-matter defects, the scratch defects, and the circuit-pattern defects, for example). Further, since the detecting pixel number of defects (i.e., the flat area of defects) are taken or memorized as one of the characteristic quantities, therefore, it is also possible to classify the category of the foreign-matter defects into the large foreign matters and the small foreign matters, as shown in FIG. 22.

Also, as those three (3) characteristic quantities, if setting up the scattered light amount from defects at high image-forming magnification, the scattered light amount from defects at low image-forming magnification, and the detecting pixel number of defects, it is possible to make classification, at least into the large foreign-matter defects and the small foreign-matter defects, easily. Also, from the characteristic quantity of the defect image, which can be obtained from the photo-detector 640, it is possible to classify the defects, such as, the fine foreign matters and/or the scratches (i.e., scratching defects), etc., on the transparent film.

Then, FIG. 24 shows the example of setting up the classification boundaries 4501 and 4502. As a method for classification, firstly the three (3) characteristic quantities mentioned above are plotted within the characteristic quantity space shown in FIG. 24 (S245 shown in FIG. 23). Then, the foreign matters belonging to the area or region divided by the classification boundaries 4501 and 4502 are classified into the category "a" (for example, the foreign-matter defects), the category "b" (for example, the scratch defects), and the category "c" (for example, the circuit-pattern defects), for example (S246 shown in FIG. 23). This FIG. 24 shows the example of classifying about thirty (30) pieces of defects into the category "a", the category "b" and the category "c", while changing the display marks thereof, for each of the defects classified into the respective categories. Thus, those classified into the category "a" (for example, the foreign-matter defects) is displayed by "○", those classified into the category "b" (for example, the scratch defects) by "▲", and those classified into the category "c" (for example, the circuit-pattern defects) by "x", respectively.

Next, explanation will be given about a method for setting up the classification boundaries, by referring to FIGS. 25(*a*) through 25(*c*). Those FIGS. 25(*a*) through 25(*c*) show two-dimensional (2D) space of characteristic quantities, in each of which one of the three (3) kinds of the characteristic quantities is set onto one (1) axis thereof, respectively. The characteristic quantity space 4601 makes up a graph for making classification from a relationship between the characteristic quantity 1 and the characteristic quantity 2, and the characteristic quantity spaces 4602 and 4603 make up graphs for making classification from relationships between the characteristic quantity 1 and the characteristic quantity 3, and between the characteristic quantity 2 and the characteristic quantity 3, respectively.

Figure 25A:
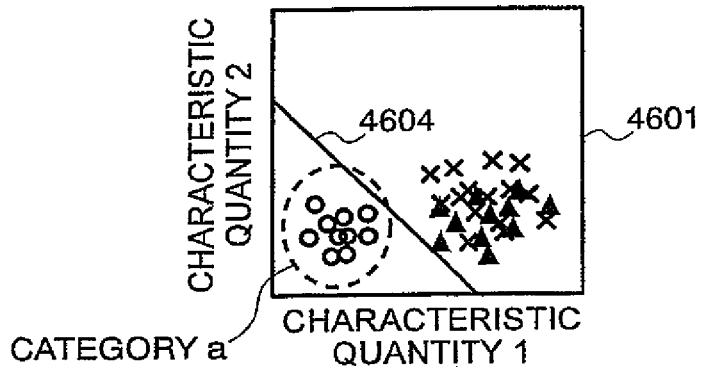
FIGS. 25(a) to 25(c) are views for explaining about a method for setting up boundaries for the classification.
Figure 25B:
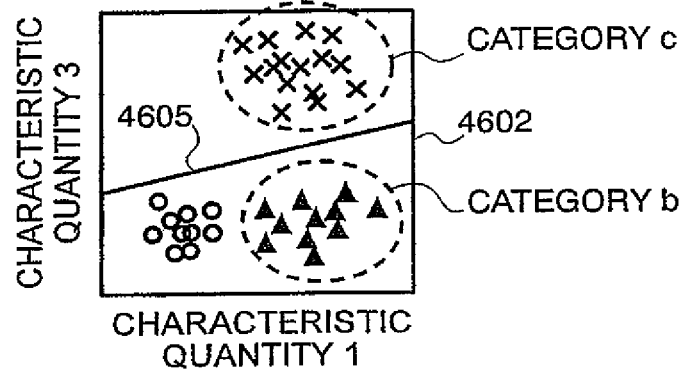
Figure 25C:
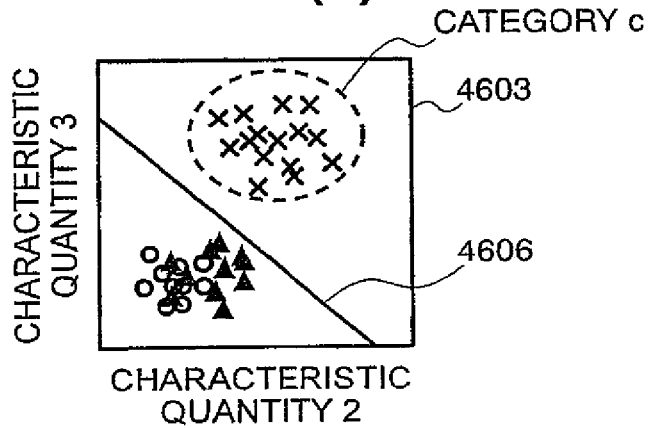

As a method for setting up the classification boundaries, firstly into the characteristic quantity spaces 4601, 4602 and 4603 are plotted the characteristic quantities of the foreign matters, the classification categories of which are already known. Herein, when making plots into the characteristic quantity spaces, the difference in the category is also presented, by changing the display mark or the like, for each of the categories thereof. For example, FIGS. 25(a) through 25(c) show examples, each displays the category "a" by "○", the category "b" by "▲", and the category "c" by "x", respectively.

Next, within those characteristic quantity spaces 4601, 4602 and 4603, the classification boundaries 4604, 4605 and 4606 are established at the position, so as to enable to divide the categories, for each. Herein, if the categories overlap in plural number thereof, there is no necessity of establishing the classification boundary between them. For example, since the category "a" is distributed at the position separated from other categories "b" and "c" within the characteristic quantity space 4601, then the classification boundary 4604 should be established for classifying the category "a" separated from the categories "b" and "c"; however, since the categories "b" and "c" overlap with each other in the distribution thereof, there is not always necessity of establishing the classification boundary between them. When conducting the classification upon the foreign matters, they are classified into the category "a" or the others, by using this characteristic quantity space 4601. In the similar manner, within the characteristic quantity spaces 4602 and 4603 are established the classification boundaries 4605 and 4606, respectively, thereby to be used when conducting the classification upon the foreign matters.

The explanation was made about the method for establishing the classification boundaries, in the above. In the present example, the explanation was given on the case of dividing the area or region into two (2) spaces by means of the classification boundary; however, when the categories are divided into three (3) or more in the distribution thereof, there may be established a plural number of classification boundaries for dividing the area or region into plural numbers thereof. Also, the classification boundary may be established with an aid of a straight line, or a curved line. Or, a user may set up the classification area or region, manually, or setting may be made through automatic calculation thereof. In the case of making setup manually, there is an advantage that the user can determine it/them arbitrarily, while in the case of making setup automatically, errors can be lowered through setting up made by a man. Herein, as a method for making setup automatically, for example, the center of gravity in the distribution is calculated out for each of the categories within one (1) piece of the characteristic quantity space, and an orthogonal bisector of a straight line connecting between the centers of gravity may be adapted to be the classification boundary. It is also possible to display a separation or isolation rate or ratio of each category together, within a space defined between the respective characteristic quantities.

Figure 26:
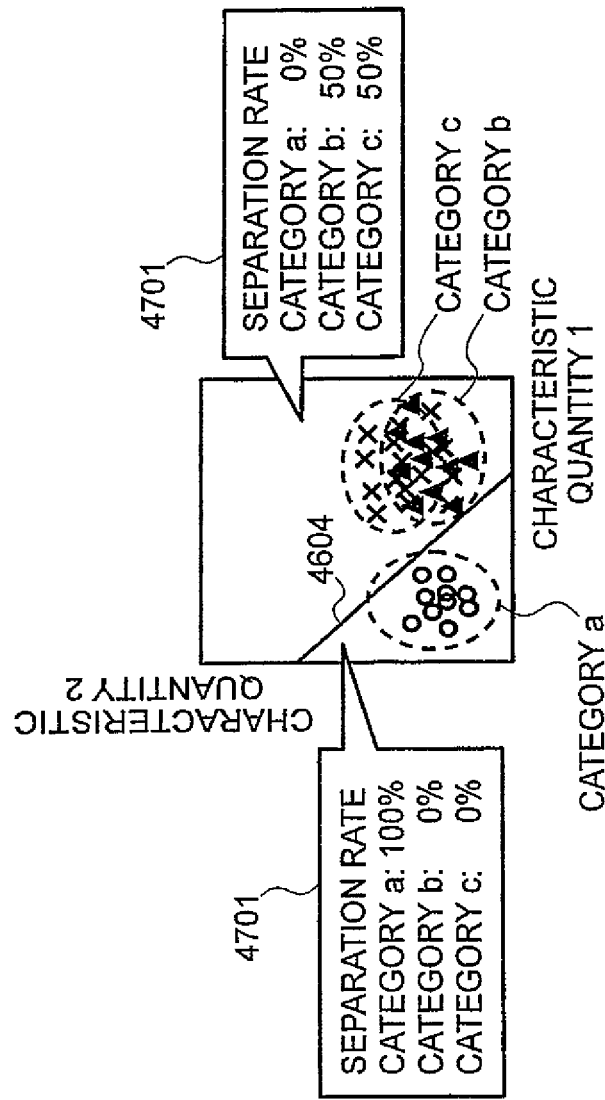
FIG. 26 is a view for showing an example of display when displaying a rate of classification.

An example of displaying the separation rate thereon is shown in FIG. 26. In this FIG. 26, a reference numeral 4701 indicates the display of the separation rate. Herein, as such the separation rate, there may be made a display on which degree the foreign matters of the same category are included within the area or region, which is separated by a separation boundary, for example. As an advantage of displaying the separation rate, it is possible for the user to grasp the separation performance of the apparatus, easily.

However, in the present embodiment, there was explained about the case of applying the characteristic quantities calculated out under the three (3) kinds of optical conditions; however, there is no necessity of restricting to the three (3) kinds thereof, always; but it may be applied into a case where the characteristic quantities are calculated out under plural kinds of optical conditions or a case where the plural numbers of characteristic quantities can be obtained under one (1) kind of the optical condition.

Next, explanation will be given about other embodiment; in particular, relating to display of the inspection result obtained from the signal processing system 40, to be displayed on the display means 52, for example, by the total controller portion 50.

Figure 27:
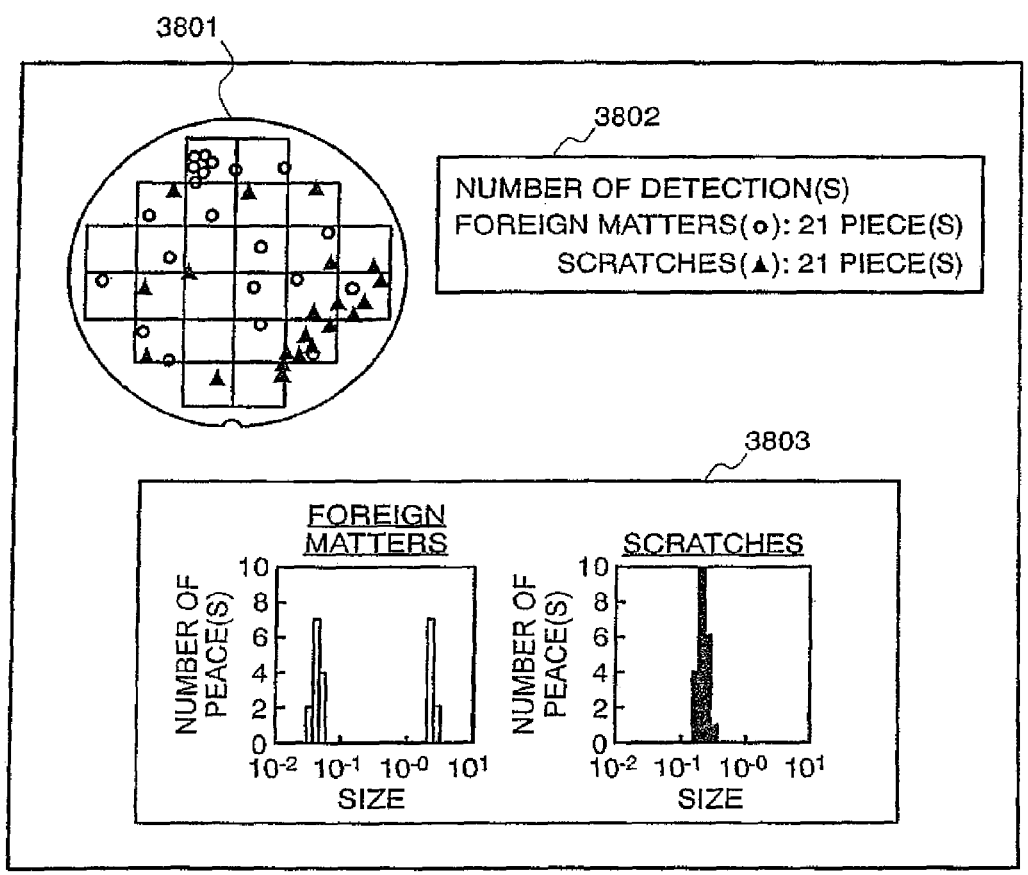
FIG. 27 is a view for showing an example of display when showing a result of classification on the defects, including the foreign matters, etc., showing a result of measurement of sizes thereof, together.

A display shown in FIG. 27 comprises position information 3801 of the foreign matters or defects detected, a detection number 3802 of the foreign matters or defects, and a histogram 3803 of sizes of the foreign matters or defects detected. However, the present embodiment shows the case where scratches are detected, as to be the defects.

In more details thereof, the position information 3801 indicates the position of the foreign matters or scratches on the wafer. However, the present embodiment shows a case where the foreign matters are indicated by "○", while the scratches by "▲". Also, the detection number 3802 is the number of pieces of the foreign matters or the scratches detected. Further, the graphs 3803 are histograms between the detection number and the sizes of the foreign matters or the scratches detected. Displaying the things detected by the defects inspecting apparatus according to the present invention, in this manner, enables the distribution of the foreign matters or the scratches to be seen at glance.

Figure 28:
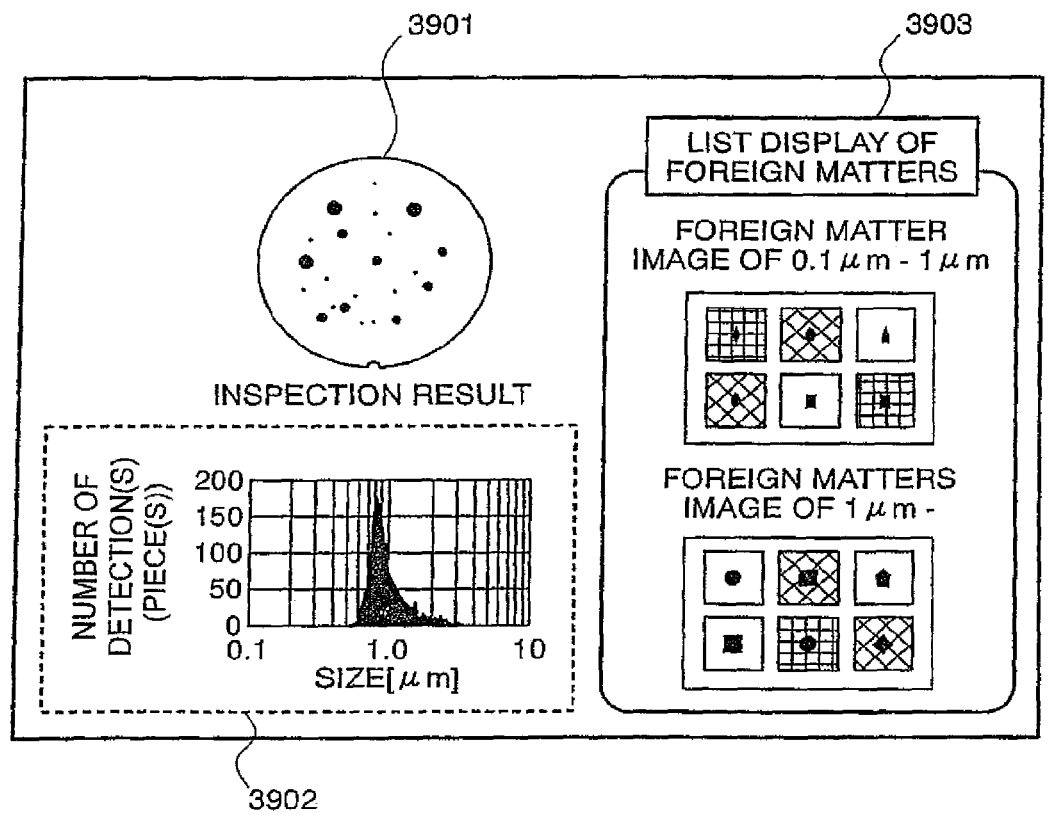
FIG. 28 is a view for showing an example of display when showing a result of measuring sizes of the defects, including the foreign matters, etc., while showing an observed image of the defects or the foreign matters, together.

A display shown in FIG. 28 comprises, an inspection map 3901 for showing the detecting positions of the detected things (i.e., of the foreign matters or the scratches), a histogram 3092 of sizes of the detected things, and a review image 3903 of the foreign matters. In the present embodiment, there is shown an example, where the total number or a part of the things detected are displayed, in relation to the inspection map 3901 and the histogram 3902. Also, in relation to the review image 3903, it is an example of displaying a view image of the things, which is detected by sampling them for each size thereof; i.e., there is shown a case of displaying six (6) pieces of the review images of foreign matters, each being equal or greater than 0.1 μm and less than 1 μm, as well as, six (6) pieces of the review images of foreign matters, each being equal or greater than 1 μm, in the present embodiment.

Herein, the review image 3903 may be an image, which can be obtained through the lights reflected and/or diffracted from the foreign matters detected by the detectors 26 and 640, or may be an image by means of an optical microscope 60 of using a white light source therein or a review apparatus of using a white light source therein, which will be mentioned later. In case of displaying the image obtained through the laser lights, it can be displayed just after completing the inspection, if the image is remained within the memory devices 53, 1302, etc., during the inspection of those detected things; therefore, there can be obtained a advantage of enabling confirmation upon the detected things, quickly. Also, in the case where the image is displayed, which is obtained through the optical microscope 60, it is enough to take an observatory image after completing the inspection, and there can be obtain an image, being clearer than the image obtained through the laser lights. In particular, when observing the foreign matters or detects less than 1 μm, and therefore it is preferable to adopt a microscope having high resolution, applying the ultra violet (UV) rays into the light source thereof.

And, it is also possible to display the position of the detected things, which are displayed on the review image 3903 mentioned above, on the inspection map 3901 together therewith.

Although the explanation was made on the case where the preview images to be displayed are six (6) pieces for each, in the present embodiment; however, there is no necessity of limiting to six (6) pieces, and therefore, the foreign matters or defects may be displayed in the total number thereof, or only of a certain rate of the number of pieces with respect to the detection number.

Figure 29:
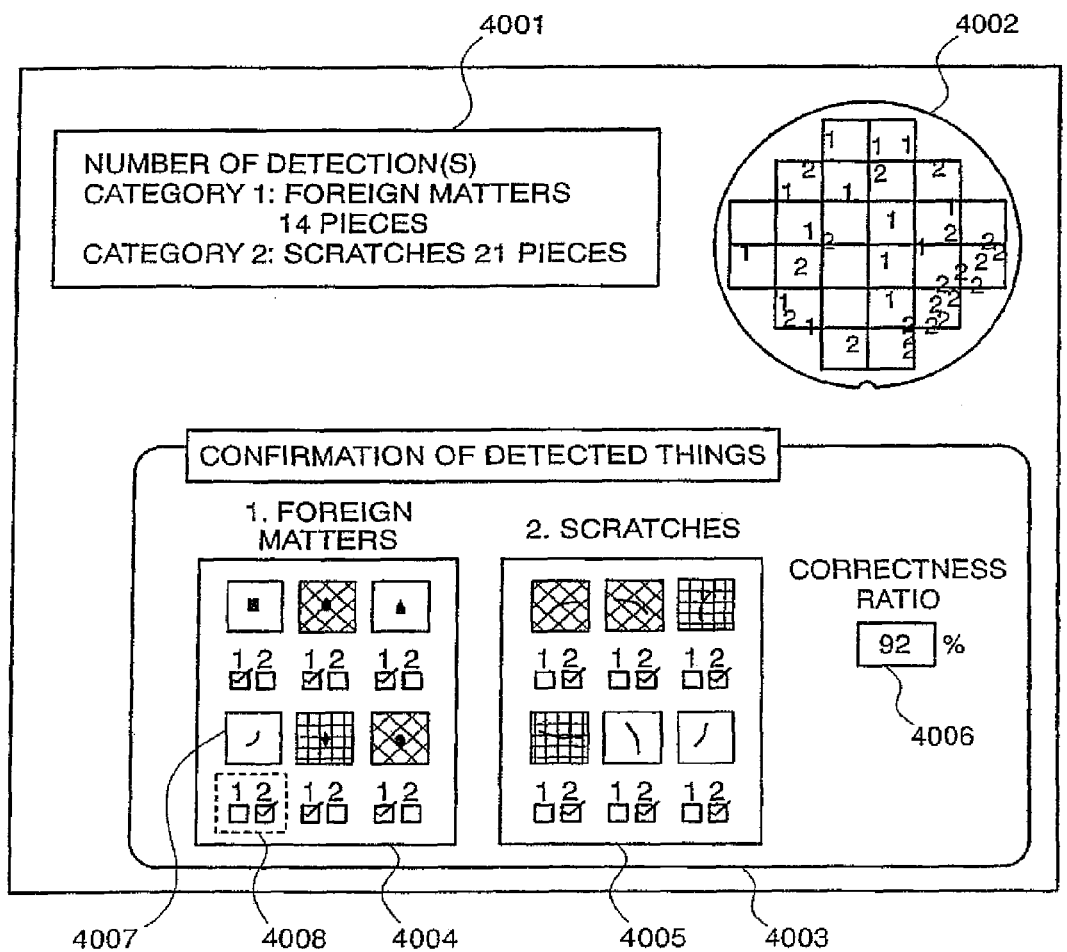
FIG. 29 is a view for showing an example, for displaying a ratio of correctness in the classification of defects, including the foreign matters, etc., upon a result of inspection thereof.

FIG. 29 shows an example of displaying the detected things, being classified into the foreign matters and the scratches, as well as, a rate or ratio of correctness of classification. This display shown in FIG. 29 comprises, detection numbers 4001 for each of the categories classified, an inspection map 4002 for showing the detecting portion of the detected things, and a confirmation screen 4003 of the detected things. The confirmation screen 4003 of the detected things, further, comprises a confirmation screen portion 4004 of the detected things, which are classified into the foreign matters by means of the defects inspecting apparatus according to the present invention, a confirmation screen portion 4005 of the detected things, which are classified into the scratches, and a classifying correctness rate display portion 4006. Those confirmation screen portions 4004 and 4005, further, comprise an observatory screen 4007 of the detected things and also a classifying-correctness determining portion 4008.

The present embodiment shows an example of classifying the things detected into two (2) categories, wherein a mark "1" indicates the foreign matters and a mark "2" the scratches, on the inspection map 4002.

Next, explanation will be made about a method for calculating out the classifying-correctness rate. First, after making the inspection by means of the defects inspecting apparatus according to the present invention, observatory images 4007 are displayed, respectively, within the confirmation image portions 4004 and 4005. In this instance, the things detected are displayed on either one of those confirmation image portions 4004 and 4005, depending upon the result of classification made within the defects inspecting apparatus according to the present invention. Next, a user of the defects inspecting apparatus, according to the present invention, inputs the categories decided by the user into the classifying-correctness determining portions 4008, which are annexed to the observatory screens 4007, respectively. In the present example, there is shown a case where checking can be made in a checkbox of the category that the user selects, as an inputting method thereof, and within the confirmation image portions 4004 of the foreign matters, ⅚ thereof is checked to be the foreign matters (i.e., the category "1") and the remaining ⅙ is checked to be the scratches (i.e., the category "2"), as an example. Also, within the confirmation image portions 4005 of the scratches, all of them are determined to be the scratches (i.e., the category "2"), in this example.

After completing the checking mentioned above, the correctness rate or ratio is displayed in the classifying-correctness rate display portion 4006. As this value is displayed a ratio of coincidence, which can be established between the classification result, which can be obtained from the defects inspecting apparatus according to the present invention, and the classification result made by the user, for example. Thereafter, in particular, with the detected things, upon which no coincidence can be made up between the classification result obtained from the defect inspecting apparatus according to the present invention and the classification result made by the user, the classifying condition of those may be renewed, by using the characteristic quantities of the said detected things, for improving an accuracy in classification.

[Total Controller Portion 50]

Figure 30:
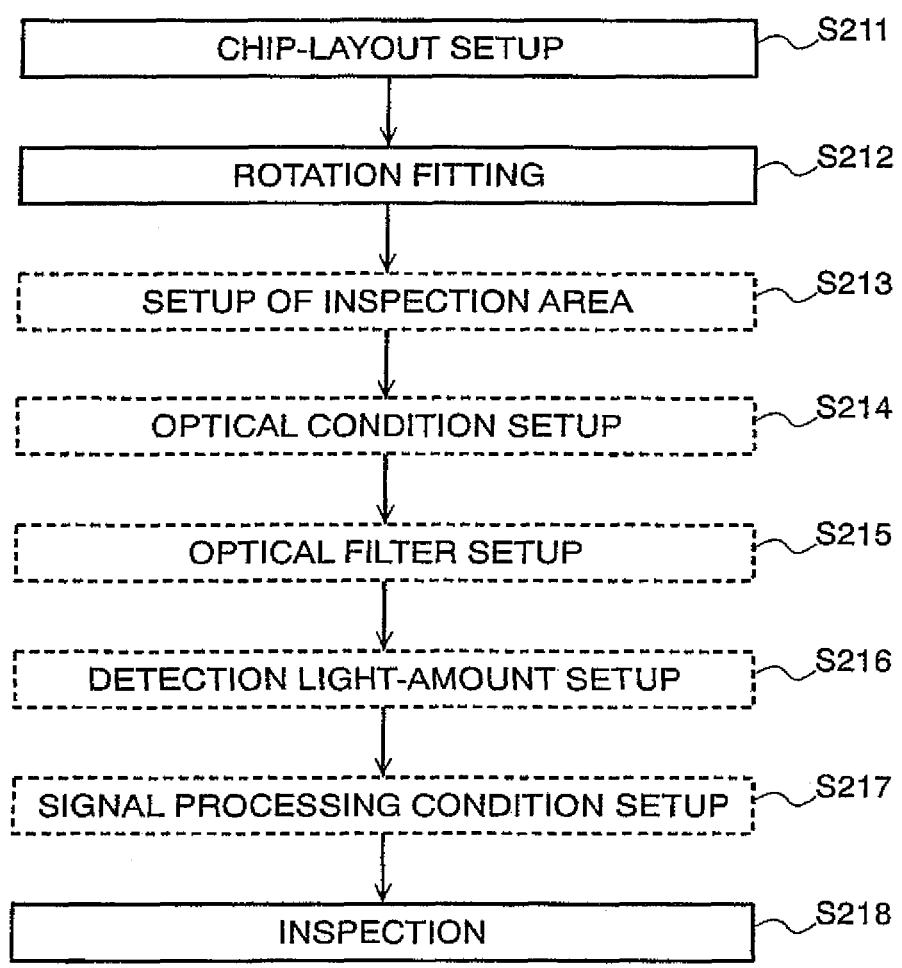
FIG. 30 is a view for showing a sequence for setting up an inspection condition, with the defects inspecting apparatus, according to the present invention.
Figure 31:
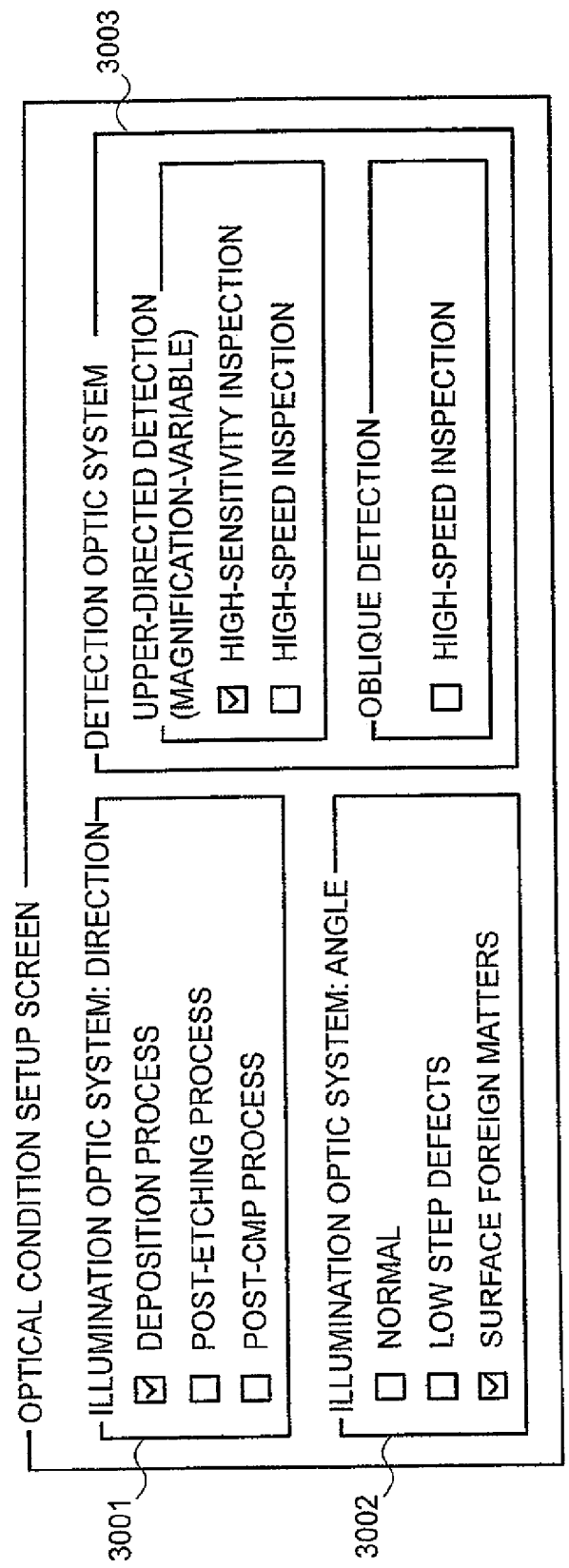
FIG. 31 is a view for explaining a screen for use of setup of an optical condition.

Next, explanation will be made about setups and so on for the inspection condition (i.e., the inspection recipe), which is executed in the total controller portion 50, etc., by referring to FIGS. 30 through 32. This FIG. 30 is a view of showing a flowchart for setting up the inspection condition (i.e., the inspection recipe). First, setup of the inspection condition (i.e., the inspection recipe), to be conducted within the total controller portion 50 before execution of inspection, comprises: setup of a chip layout (S211), rotation fitting on the inspection target (S212), setup of the inspection area (S213), setup of the optical condition (S214), setup of the optical filter (S215), setup of detected light amount (S216), and setup of the signal processing condition (S217). Further, S218 is an actual execution of an inspection.

Next, explanation will be made about each of those setups, which are executed by the total controller portion 50. First, in the setup of a chip layout (S211), chip sizes and/or presence or non-presence of chips on the wafer are set into the signal processing system 40, with using CAD information or the like, within the total controller portion 50. This chip size is necessary to be set up, since it means the distance for conducting comparison process thereupon. Next, the rotation fitting (S212) is the setup for bringing the aligning direction of chips on the wafer 1 mounted on the stage and the pixel direction of the photo-detector 26 in parallel with each other, i.e., rotating the wafer 1 so as to adjust the rotation shift to be almost "0". Since conduction of this rotation fitting brings the repetitive patterns on the wafer to be aligned on one (1) axis direction, the chip-comparison signal process can be conducted, with easiness. Next, in the setup of inspection area or region (S213), setting is made on the position where the inspection should be made on the wafer, and on the detection sensitivity within that inspection area, for the total controller portion 50 to controls the signal processing system 40. Conducting this inspection area setup (S213) enables the inspection at the optimal sensitivity upon each of the areas on the wafer. The setting method thereof is as was mentioned, by referring to FIG. 15 in the above.

Next, the inspection condition setup (S214) means selection on the direction and the angle of illumination lights irradiated upon the wafer, and/or selection on the magnifying power of the magnification-variable detection optic system 20, for the total controller 50 to make control upon the illumination optic system 10 and the magnification-variable detection optic system 20. As a selecting method, for example, the setup can be achieved by using an optical condition setup window as shown in FIG. 31, for example. The said optical condition setup screen comprises an illumination direction condition 3001 for the illumination system, an illumination angle condition 3002 for the illumination system, and a detection optic system condition 3003 (including the detection direction, such as, the upper-directed one or the oblique one, for example). In this FIG. 31 is shown an example, on which the selection can be made among three (3) kinds on the illumination direction condition 3001, three (3) kinds on the illumination angle condition 3002, and between two (2) kinds on the detection optic system condition 3003. A user of the present defects inspecting apparatus can make selection of the optimal condition while watching the contents of the conditions 3001, 3002 and 3003, appropriately. For example, when she/he wishes to make an inspection on the foreign matters on the surface thereof at high sensitivity, if the inspection target 1 is a wafer during a metal-film deposition process, then it is enough to select "deposition process" from conditions within the illumination direction condition 3001, further select "surface foreign matters" from conditions within the illumination angle condition 3002, and select "upper-directed detection (magnification-variable): high sensitivity inspection" from conditions within detection optic system condition 3003; and an example of conducting those selections is shown in FIG. 31. Also, when she/he wishes to make an inspection upon the defects, such as, the foreign matters and/or the scratches, if the inspection target is the oxidation film, for example, then it is enough to select "CMP post-process" from conditions within the illumination direction condition 3001, and further select "surface foreign matters" from conditions within the illumination angle condition 3002, and select "oblique detection: high speed inspection" from conditions within detection optic system condition 3003.

Next, the optical filter setup (S215) is for setting up the space filter 22 shown in FIG. 1 and/or the optical filter 24b, such as, of a polarizing element or the like, for the total controller portion 50 to make control upon the detection optic system 200, etc. This space filter 22 is one for shielding the lights reflected and/or diffracted from the repetitive patterns manufacture on the wafer; therefore, it is preferable to be set up for the wafer having the repetitive patterns, but no necessity to be set up for the wafer having no such repetitive pattern thereon. Also, the polarizing element 24b is effective if it is used in the situation where edges of wiring patters are etched in vicinity of a right angle, for example.

Next, the detection light amount setup (S216) is a sep for adjusting the light amount to be incident upon the photo-detector 26, for the total controller portion 50 to make control upon the illumination optic system 10 or the magnification-variable detection optic system 20. The lights reflected and scattered from the circuit patterns manufactured on the wafer changes the components to be diffracted thereupon, depending upon the configuration of the circuit pattern. In more details, in a case when the wafer surface is flat, the scattered lights are hardly generated thereupon; i.e., almost of those comes to be the regular reflection lights. On the contrary to this, if concave and convex are large on the wafer surface, then the scattered lights are generated thereon much. Accordingly, the lights reflected and/or diffracted from the circuit patterns change depending upon the condition of the wafer surface, i.e., the manufacturing process of devices. However, due to presence of the dynamic range on the photo-detector 26, therefore it is preferable to adjust the light amount to be incident upon in conformity with that dynamic range. For example, it is preferable so that the amount of lights reflected and/or diffracted from the circuit patterns on the wafer comes down to be about 1/10 of the dynamic range of the photo-detector 26. Herein, as a method for adjusting the light amount incident upon the photo-detector 26, it may be achieved through adjustment of an amount of the output lights from the laser-light source 11, or it may be adjusted with using the ND filter 24a.

Next, the signal processing condition setup (S217) is for making setup for detection condition of the defects, such as, foreign matters, etc., for the total controller portion 50 to make control upon the signal processing system 40.

After completing the setups mentioned above, the user can conduct the inspection under the desired condition by conducting the inspection process (S218).

However, as a method for setting up the details, which are explained in the present embodiment, for example, the details may be inputted from design information of the inspection target by hands, or may be inputted with using an input assist function equipped with the foreign-matter inspecting apparatus according to the present invention, or information may be obtained from an upper system through a network.

Further, among those setups mentioned above, in particular, the inspection area or region (S213), the inspection condition setup (S214), the optical filter setup (S215), the detection light amount setup (S216) and signal processing condition setup (S217) are not necessarily changed depending upon the inspection target, always, but they may be a certain value irrespective of the inspection target. If setting those at a certain value, it is possible to shorten the time for setting the inspection conditions; however, for obtaining the high sensitivity, it is desirable to make a tuning upon each of the inspection conditions. Also, there is no necessity of conducting it on the inspection area or region (S213) before the inspection condition setup (S214), always; but it may be set up before the inspection process (S218).

Figure 32:
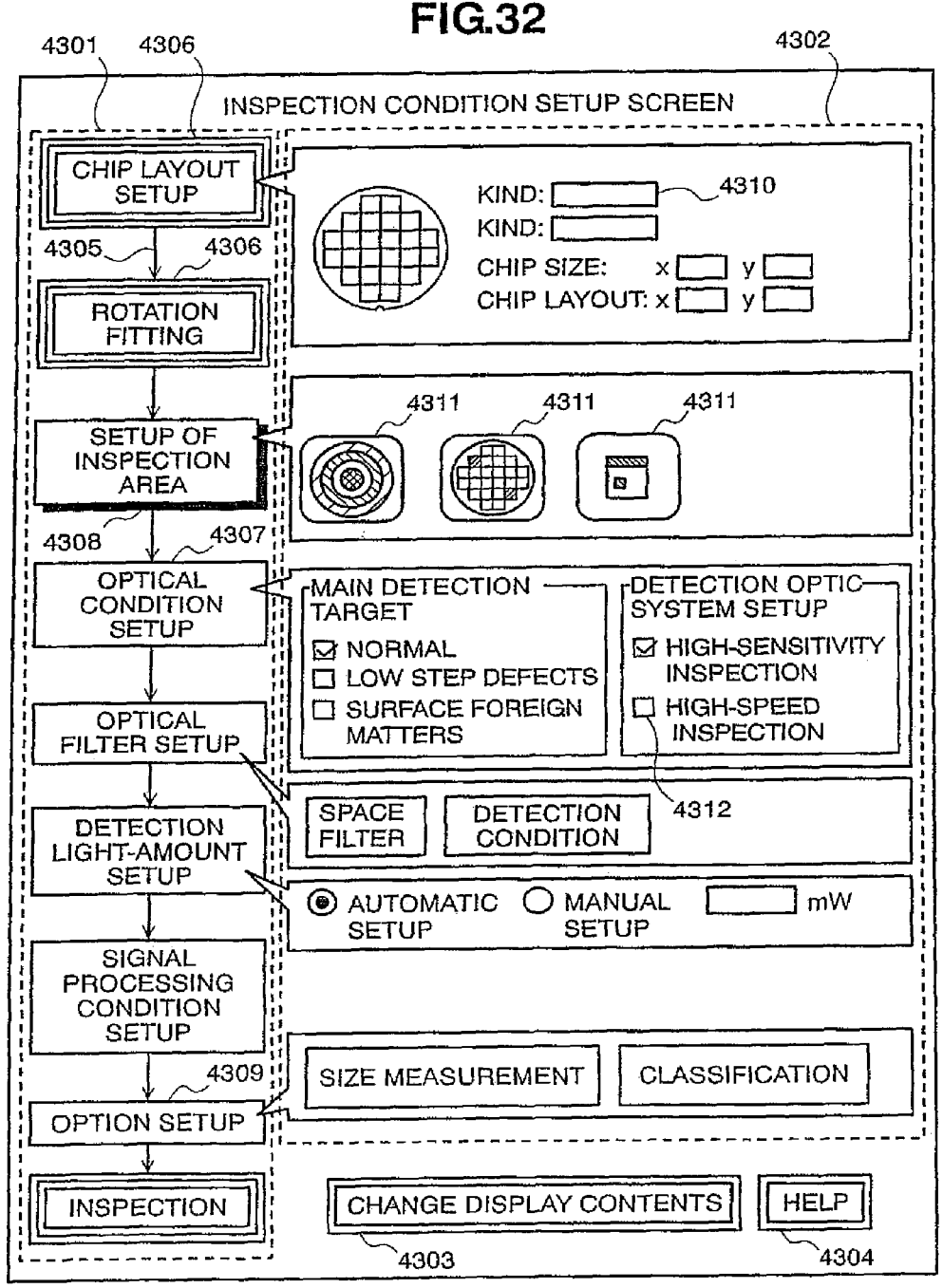
FIG. 32 is a view for explaining a screen for use of setup of an inspection condition.

An example of a screen is shown in FIG. 32, for use of setting up the contents, which are explained in the above. This screen shown in FIG. 32 comprises a condition setup sequence 4301, detailed conditions 4302 for contents of the each setup, a setup-contents display change button 4303, and a help button 4304.

Next, the details thereof will be given. First, the condition setup sequence 4301 shows a flow of the setups of inspection conditions within the foreign-matter inspecting apparatus according to the present invention. A user may set up the conditions in series from the "chip layout setup" within the condition setup sequence 4301.

The characteristic of the condition setup sequence 4301 lies in that indication by arrows 4305 of condition settings enables the user to make the settings through the shortest sequence, but without an error. Also, as other characteristics thereof, items are separated into those necessary to be established and others not so; in other words, those to be established, necessarily, and others, each may be set at a predetermined value. Separation of the indications enables the user to see the minimum items to be set. For example, when the user needs the inspection result soon, she/he may set only the necessary items to be setup, or when willing to make a tuning on the detection sensitivity, for example, she/he may set up the condition about the items, buy not necessary to be set; therefore, degree of settings can be changed depending on desire of the user. For example, in this embodiment, a button 4306 displayed by triplicate frames around it indicates that it is an item, which must be established, necessarily, while a button 4307 displayed by a single frame around it indicates that it is an item, being low in the necessity of setting thereof. Further, as other characteristics, a clear indication is made, for the user to know which item she/he is now setting up. For example, a button 4308 is displayed attaching the shade therewith, to be distinguished from the buttons 4306 and 4307. In this manner, clear indication of the position at present brings about an advantage that the user can see the number of remaining items to be set up at glance.

However, the present embodiment shows an example of adding an option condition setup 4309 to the sequence explained by referring to FIG. 30. The details of this option condition setup 4309 include, for example, setup of a size measuring function of foreign matters, and/or a setup of classifying condition of foreign matters and/or defects.

Next, detailed conditions 4302 are a screen for establishing the details of each of the conditioning items. As a method for inputting or selecting the items, it may be provided with a place to be inputted through a keyboard, for example, in the form of an input box 4310, or may be applied a method of selecting an input item with an aid of an icon, for example, in the form of an input icon 4311. However, the input icon 4311 is an example of indicating the respective icons for three (3) kinds of input items, wherein another window comes out when pushing down one of those icons, so as to enable condition setup of the details. Furthermore, it may be a method of selecting a necessary item, such as, an input check box 4312, for example.

Also, the setout-contents display change button 4303 is that for making change or customizing the display items. For example, when there is an item, on which the user always wishes to establish, or with which she/he wishes to increase the number of setting contents, this setout-contents display change button 4303 enables the user to make such changes thereupon; therefore, the user can obtain an easy screen to use, to establish the inspection conditions, as quickly as possible. Further, the help button 4304 is for letting information to be outputted, for the purpose of aiding the user when she/he looses the way of setting and/or cannot understand the contents of setting. As a method thereof, the contents of the each setup item may be announced in the form of voice guidance, or an operation method may be displayed through the moving picture of MPEG, etc. Or, it is also possible for the user to talk with a designer of a maker, who produces the foreign-matter inspecting apparatus according to the present invention, on line, via a network or a telephone circuit.

Embodiment Equipped with Microscope

Figure 33:
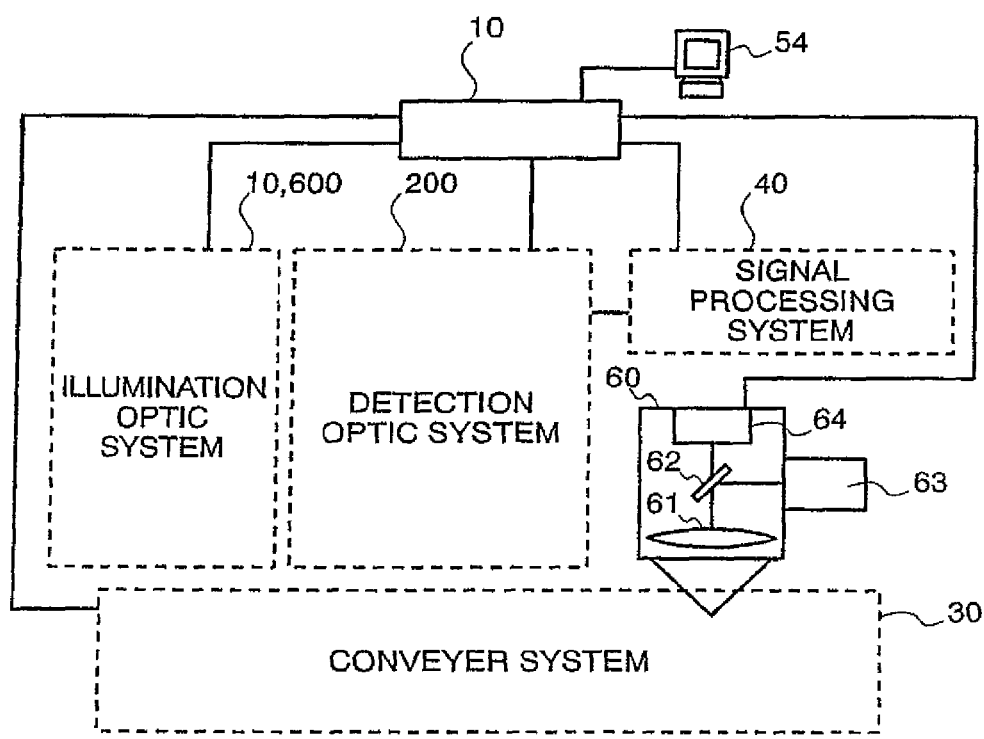
FIG. 33 is a view for showing the brief structure of an embodiment, on which an observatory optic microscope is equipped with, according to the present invention.

Explanation will be made about an embodiment, in relation to the defects inspecting apparatus equipped with an observatory optical microscope, according to the present invention, by referring to FIGS. 1 and 33. In the present embodiment, an observatory optical microscope 60, comprising an objection lens 61, a half-mirror 62, a light source 63 and a TV camera 64, is provided in parallel with the illumination optic system 10 and the detection optic system 200. This observatory optical microscope 60 is provided for the purpose of moving the defects (including false information) of foreign matters, etc., on the wafer 1, which are detected through the signal processing system 40 of the defects inspecting apparatus and memorized into the memory device 53, for example, within a view field of the detection optic system 61-63 of the observatory optical microscope 60, through movement of the stages 31 and 32.

A merit of provision of the observatory optical microscope 60 in parallel with lies in that the defects, such as, the foreign matters, which are detected through the signal processing system 40 of the defects inspecting apparatus, can be observed immediately, enlargedly, only through the movement of the stages 31 and 32, but without moving the wafer onto the review apparatus, such as, the SEM, etc. In this manner, the immediate and enlarged observation of the detected things through the defects inspecting apparatus enables quick identification of reasons of generating the defects, such as, foreign matters, etc.

Figure 34:
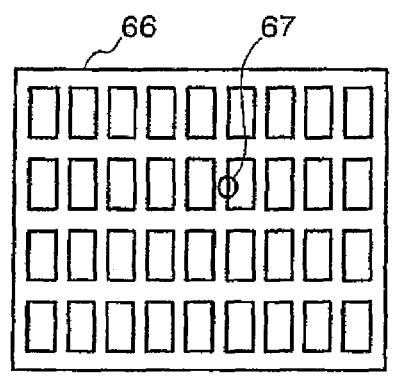
FIG. 34 is a view for showing a screen, which can be observed through the observatory optic microscope shown in FIG. 33.

However, displaying an image thereof, which is picked up by the TV camera 64 of the observatory optical microscope 60, enlargedly, as a screen 66 shown in FIG. 34, on a color monitor 54 or 52, in common use with a personal computer, for example, but there sometimes occur cases where the defects cannot be seen well, to be identified with the cause of generation thereof, i.e., the things detected through the defects inspecting apparatus, depending on the kinds thereof, due to existence of the circuit patterns. Then, since the total controller portion 50 can display the image, for example, in the form of 256×256 lines of pixels, on the display device 52, together with an image of the defects, which are memorized into the data memory portion 1302 or the memory device 53, after being classified within the inspection-result integration processor portion 1309 of the signal processing system 40 and detected on the respective position coordinates thereof, it is possible to identify the position on an enlarged image taken by the TV camera 64 of the observatory optical microscope 60, upon basis of the position coordinates and the image of that defects. As a result of this, within the observatory optical microscope 60, an area or a mark 67 indicative of the identified defects mentioned above is displayed on the screen 66 of the color monitor 54 or 52, and upon designation of that area or mark 67 displayed, the defects are put within the view field of the detection optic system 61-63 through movement of the stages 31 and 32; thereby enabling the enlarged observation of the defects, immediately, even at the position where the defects cannot be seen easily. In brief, since the position coordinates and the image of the defects, to be analyzed in the details thereof, can be detected through the signal processing system 40 upon basis of the defects image signal, which is detected from the detection optic system 200, therefore, the detailed analysis can be also made even on that defects, which cannot be seen easily, upon identification of the area or mark 67 indicative of that defects on the enlarged image, which is picked up by the TV camera 64 upon basis of the position coordinates and image of that defects detected, through the observatory optical microscope 60, in the similar manner to the review apparatus, and as a result thereof, it is possible to estimate the cause of generation of that defects. Of course, since on the color monitor 54 or 52 is displayed the area or mark 67 indicative of the defects identified, it is also possible to confirm on whether the detection optic system 200 and the signal processing system 40 actually detects the defects or not, on a side of the observatory optical microscope 60.

Further, the observatory optical microscope 60 may be a microscope having the light source 63 of visible lights (for example, a white light), or may be another microscope having the light source 63 of ultra-violet (UV) lights. In particular, for making an observation upon the very fine or microscopic foreign matters of 0.1 μm, in the level thereof, it is preferable to use the microscope having high resolution, such as, applying the ultra-violet (UV) lights therein. Or, using the microscope of applying the visible lights therein brings about an advantage that, color information can be obtained from, and the foreign matters can be acknowledged easily.

INDUSTRIAL APPLICABILITY

According to the present invention, it is possible to make an inspection of defects, such as, fine or microscopic foreign matters and/or scratches, etc., of a level of 0.1 μm, upon an inspection target substrate, upon the surface of which is formed a transparent film, such as, oxidation films, etc., and/or an inspection target substrate, on the surface of which repetitive patterns are mixed up with non-repetitive patterns, at high sensitivity and high seed.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraces therein.

What is claimed is:

1. A defect inspecting apparatus, comprising:
   an illumination optic system configured to irradiate slit-like shaped laser beams upon a surface of an inspection target substrate;
   a detection optic system, having a first detector and a second detector configured to detect light initially radiated from said illumination optic system and thereafter scattering upon the surface of said inspection target substrate, the second detector being disposed in a direction different from that of said first detector, with respect to the surface of said inspection target substrate; and a processing portion configured to compare a first characteristic quantity upon basis of a first scattering light detected by said first detector of said detecting optic system, and a second characteristic quantity upon basis of a second scattering light detected by said second detector of said detection optic system, and thereby conducting a classification of defects;

wherein said first scattering light is detected under an optical condition differing from said second scattering light, in at least one of: an illumination angle of said illumination optic system, a direction of illumination of said illumination optic system, a detection angle of said detection optic system, an intersection angle of said detection optic system, a magnification of said detection optic system, or an optical filter of said detection optic system.

2. The defect inspecting apparatus, as described in the claim 1, wherein
a first defect is extracted with using said first characteristic quantity and a second defect is extracted with using said second characteristic quantity within said processing portion.

3. The defect inspection apparatus, as described in the claim 1, wherein
said second characteristic quantity includes a characteristic quantity upon basis of the scattering light scattering from a position of said first defect.

4. A defect inspecting method, comprising the following steps of:
an illuminating step that irradiates slit-like shaped laser beams upon a surface of an inspection target substrate;
a first detecting step having a first detecting step that detects light initially radiated in said illuminating step and thereafter scattering upon the surface of said inspection target substrate into a first direction;
a second detecting step that detects light scattering into a second direction differing from said first detection;
a processing step that compares: a first characteristic quantity upon basis of a first scattering light detected in said first detecting step, and a second characteristic quantity upon basis of a second scattering light detected in said second detecting step, and thereby conducting a classification of defects;
wherein said first scattering light is detected under an optical condition differing from said second scattering light, in at least one of: an illumination angle in said illuminating step, a direction of illumination in said illuminating step, a detection angle in said detecting step, an intersection angle in said detecting step, a magnification in said detecting step, or an optical filter in said detecting step.

5. The defect inspecting method, as described in the claim 4, wherein
a first defect is extracted with using said first characteristic quantity and a second defect is extracted with using said second characteristic quantity in said processing step.

6. The defect inspecting method, as described in the claim 4, wherein
said second characteristic quantity includes a characteristic quantity upon basis of the scattering light scattering from a position of said first defect.

7. The defect inspecting apparatus, as described in the claim 1,
wherein said optical condition, which differs for said first scattering light in comparison to said second scattering light, comprises an illumination angle of said illumination optic system.

8. The defect inspecting apparatus, as described in the claim 1,
wherein said optical condition, which differs for said first scattering light in comparison to said second scattering light, comprises a direction of illumination of said illumination optic system.

9. The defect inspecting apparatus, as described in the claim 1,
wherein said optical condition, which differs for said first scattering light in comparison to said second scattering light, comprises a detection angle of said detection optic system.

10. The defect inspecting apparatus, as described in the claim 1,
wherein said optical condition, which differs for said first scattering light in comparison to said second scattering light, comprises an intersection angle of said detection optic system.

11. The defect inspecting apparatus, as described in the claim 1,
wherein said optical condition, which differs for said first scattering light in comparison to said second scattering light, comprises a magnification of said detection optic system.

12. The defect inspecting apparatus, as described in the claim 1,
wherein said optical condition, which differs for said first scattering light in comparison to said second scattering light, comprises an optical filter of said detection optic system.

13. The defect inspecting method, as described in the claim 4,
wherein said optical condition, which differs for said first scattering light in comparison to said second scattering light, comprises an illumination angle in said illuminating step.

14. The defect inspecting method, as described in the claim 4,
wherein said optical condition, which differs for said first scattering light in comparison to said second scattering light, comprises a direction of illumination in said illuminating step.

15. The defect inspecting method, as described in the claim 4,
wherein said optical condition, which differs for said first scattering light in comparison to said second scattering light, comprises a detection angle in said detecting step.

16. The defect inspecting method, as described in the claim 4,
wherein said optical condition, which differs for said first scattering light in comparison to said second scattering light, comprises an intersection angle in said detecting step.

17. The defect inspecting method, as described in the claim 4,
wherein said optical condition, which differs for said first scattering light in comparison to said second scattering light, comprises a magnification in said detecting step.

18. The defect inspecting method, as described in the claim 4, wherein said optical condition, which differs for said first scattering light in comparison to said second scattering light, comprises an optical filter in said detecting step.

* * * * *